United States Patent
Nazarenko (10) Patent No.: US 9,605,303 B2
(45) Date of Patent: Mar. 28, 2017

(54) METHOD OF DETERMINING AND CONFIRMING THE PRESENCE OF AN HPV IN A SAMPLE

(75) Inventor: Irina Nazarenko, Gaithersburg, MD (US)

(73) Assignee: QIAGEN GAITHERSBURG, INC., Gaithersburg, MD (US)

( * ) Notice: Subject to any disclaimer, the term of this patent is extended or adjusted under 35 U.S.C. 154(b) by 1334 days.

(21) Appl. No.: 13/016,004

(22) Filed: Jan. 28, 2011

(65) Prior Publication Data

US 2011/0294111 A1   Dec. 1, 2011

Related U.S. Application Data

(60) Provisional application No. 61/299,729, filed on Jan. 29, 2010.

(51) Int. Cl.
C12Q 1/68    (2006.01)
C12Q 1/70    (2006.01)

(52) U.S. Cl.
CPC ......... *C12Q 1/6827* (2013.01); *C12Q 1/6813* (2013.01); *C12Q 1/708* (2013.01)

(58) Field of Classification Search
None
See application file for complete search history.

(56) References Cited

U.S. PATENT DOCUMENTS

| | | |
|---|---|---|
| 4,486,536 A | 12/1984 | Baker et al. |
| 4,486,539 A | 12/1984 | Ranki et al. |
| 4,563,417 A | 1/1986 | Alabrella et al. |
| 4,563,419 A | 1/1986 | Ranki et al. |
| 4,689,294 A | 8/1987 | Boguslawski et al. |
| 4,731,325 A | 3/1988 | Palva et al. |
| 4,732,847 A | 3/1988 | Stuart et al. |
| 4,743,535 A | 5/1988 | Carrico |
| 4,751,177 A | 6/1988 | Stabinsky et al. |
| 4,775,619 A | 10/1988 | Urdea |
| 4,833,084 A | 5/1989 | Carrico |
| 4,851,330 A | 7/1989 | Kohne et al. |
| 4,865,980 A | 9/1989 | Stuart et al. |
| 4,868,105 A | 9/1989 | Urdea et al. |
| 4,889,798 A | 12/1989 | Rabbani |
| 4,894,325 A | 1/1990 | Englehardt et al. |
| 5,082,830 A | 1/1992 | Brakel et al. |
| 5,106,727 A | 4/1992 | Hartley et al. |
| 5,116,734 A | 5/1992 | Higgs et al. |
| 5,200,313 A | 4/1993 | Carrico |
| 5,288,611 A | 2/1994 | Kohne et al. |
| 5,374,524 A | 12/1994 | Miller et al. |
| 5,424,413 A | 6/1995 | Hogan et al. |
| 5,437,977 A | 8/1995 | Segev |
| 5,474,895 A | 12/1995 | Ishii et al. |
| 5,484,699 A | 1/1996 | Bouma et al. |
| 5,545,806 A | 8/1996 | Lonberg et al. |
| 5,545,807 A | 8/1996 | Surani et al. |
| 5,556,748 A | 9/1996 | Douglas |
| 5,614,362 A | 3/1997 | Urdea et al. |
| 5,623,049 A | 4/1997 | Lobberding et al. |
| 5,627,030 A | 5/1997 | Pandian et al. |
| 5,629,153 A | 5/1997 | Urdea |
| 5,629,156 A | 5/1997 | Shah et al. |
| 5,635,352 A | 6/1997 | Urdea et al. |
| 5,641,630 A | 6/1997 | Snitman |
| 5,656,731 A | 8/1997 | Urdea |
| 5,681,697 A | 10/1997 | Urdea et al. |
| 5,681,897 A | 10/1997 | Silvis et al. |
| 5,695,926 A | 12/1997 | Cros et al. |
| 5,702,893 A | 12/1997 | Urdea et al. |
| 5,728,531 A | 3/1998 | Yamada et al. |
| 5,731,153 A | 3/1998 | Lucas et al. |
| 5,736,316 A | 4/1998 | Irvine et al. |
| 5,747,244 A | 5/1998 | Sheridan et al. |
| 5,747,248 A | 5/1998 | Collins |
| 5,750,338 A | 5/1998 | Collins et al. |
| 5,759,773 A | 6/1998 | Tyagi et al. |
| 5,786,183 A | 7/1998 | Ryder et al. |
| 5,792,606 A | 8/1998 | Deger et al. |
| 5,800,994 A | 9/1998 | Martinelli et al. |
| 5,814,492 A | 9/1998 | Carrino et al. |

(Continued)

FOREIGN PATENT DOCUMENTS

| | | |
|---|---|---|
| CN | 1690223 A | 11/2005 |
| CN | 101177701 A | 5/2008 |

(Continued)

OTHER PUBLICATIONS

Zientara et al., 1998 "Use of reverse transcriptase-polymerase chain reaction (RT-PCR) and dot-blot hybridization for the detection and identification of African horse sickness virus nucleic acids" Arch Virol 14:317-327.

Mansy et al., 1999 "A PCR Based DNA Hybridisation Capture System for the Detection of Human Cytomegalovirus. A Comparative Study with Other Identification Methods" Journal of Virological Methods 80:113-122.

Poulsen et al., 1999 "Detection of Clinical Vancomycin-Resistant Enterococci in Denmark by Multiplex PCR and Sandwich Hybridization" APMIS 107:404-12.

Sjoroos et al., 1998 "Time-Resolved Fluorometry Based Sandwich Hybridisation Assay for HLA-DQA1 Typing" Disease Markers 14:9-19.

Edman et al., 2000 "Pathogen Analysis and Genetic Predisposition Testing Using Microelectronic Arrays and Isothermal Amplification" Journal of Investigative Medicine, 48:93-101.

(Continued)

*Primary Examiner* — Prabha Chunduru
(74) *Attorney, Agent, or Firm* — McBee Moore Woodward & Vanik IP, LLC.

(57) ABSTRACT

Methods are provided for genotyping a target nucleic acid in a sample. In various aspects, the methods comprise generating nucleic acid hybrids between probes specific for the genotypes of interest and the target nucleic acid and detecting hybridization in the sample. In other aspects, the methods comprise using multi-probe mixtures to reduce the volume of sample necessary to determine the genotype of the target nucleic acid.

14 Claims, 3 Drawing Sheets

(56) References Cited

U.S. PATENT DOCUMENTS

| | | | |
|---|---|---|---|
| 5,821,339 A | 10/1998 | Schafer et al. | |
| 5,827,661 A | 10/1998 | Blais | |
| 5,853,993 A | 12/1998 | Dellinger et al. | |
| 5,888,724 A | 3/1999 | Silverstein et al. | |
| 5,981,179 A | 11/1999 | Lorincz et al. | |
| 5,994,079 A | 11/1999 | De La Rosa et al. | |
| 6,010,895 A | 1/2000 | Deacon et al. | |
| 6,027,897 A | 2/2000 | Lorincz et al. | |
| 6,043,038 A | 3/2000 | Sivaraja et al. | |
| 6,057,099 A | 5/2000 | Nathan et al. | |
| 6,083,925 A | 7/2000 | Li et al. | |
| 6,110,676 A | 8/2000 | Coull et al. | |
| 6,110,682 A | 8/2000 | Dellinger et al. | |
| 6,110,687 A | 8/2000 | Nilsen | |
| 6,207,385 B1 | 3/2001 | Stanley | |
| 6,221,581 B1 | 4/2001 | Engelhardt et al. | |
| 6,225,053 B1 | 5/2001 | Garcia et al. | |
| 6,228,578 B1 | 5/2001 | Impraim et al. | |
| 6,228,580 B1 | 5/2001 | Blumenfeld et al. | |
| 6,232,462 B1 | 5/2001 | Collins et al. | |
| 6,268,128 B1 | 7/2001 | Collins et al. | |
| 6,277,579 B1 | 8/2001 | Lazar et al. | |
| 6,280,954 B1 | 8/2001 | Ulfendahl | |
| 6,326,136 B1 | 12/2001 | Lazar et al. | |
| 6,355,424 B1 | 3/2002 | Lorincz et al. | |
| 6,436,662 B1 | 8/2002 | Mielzynska et al. | |
| 6,521,190 B1 | 2/2003 | Edens et al. | |
| 6,544,732 B1 | 4/2003 | Chee et al. | |
| 6,583,278 B1 | 6/2003 | Carter | |
| 6,686,151 B1 | 2/2004 | Lazar et al. | |
| 6,828,098 B2 | 12/2004 | Langmore et al. | |
| 6,890,729 B2 | 5/2005 | Mielzynska et al. | |
| 6,969,585 B2 | 11/2005 | Lorincz et al. | |
| 6,977,148 B2 | 12/2005 | Dean et al. | |
| 7,001,776 B2 | 2/2006 | Botacini das Dores et al. | |
| 7,371,518 B2 | 5/2008 | Lorincz et al. | |
| 7,439,016 B1 * | 10/2008 | Anthony et al. | 435/6.1 |
| 7,601,497 B2 | 10/2009 | Nazarenko et al. | |
| 7,812,144 B2 | 10/2010 | Karlsen | |
| 8,012,944 B2 | 9/2011 | Lacasse et al. | |
| 2001/0055766 A1 | 12/2001 | Aristarkhov et al. | |
| 2002/0012936 A1 | 1/2002 | Lorincz et al. | |
| 2003/0096232 A1 | 5/2003 | Kris et al. | |
| 2003/0108897 A1 | 6/2003 | Drmanac | |
| 2003/0175765 A1 | 9/2003 | Kessler et al. | |
| 2003/0175789 A1 | 9/2003 | Weininger et al. | |
| 2004/0180362 A1 | 9/2004 | Lazar et al. | |
| 2004/0214302 A1 | 10/2004 | Anthony et al. | |
| 2005/0026976 A1 | 2/2005 | Curtin et al. | |
| 2005/0032038 A1 | 2/2005 | Fisher et al. | |
| 2005/0032105 A1 | 2/2005 | Bair et al. | |
| 2005/0119217 A1 | 6/2005 | Lacasse et al. | |
| 2005/0147996 A1 | 7/2005 | Sorge | |
| 2006/0051809 A1 * | 3/2006 | Nazarenko et al. | 435/6 |
| 2006/0160188 A1 | 7/2006 | Kurnit et al. | |
| 2006/0240449 A1 | 10/2006 | McGlennen et al. | |
| 2007/0109898 A1 | 5/2007 | Kasai | |
| 2007/0154884 A1 | 7/2007 | Lorincz | |
| 2007/0292899 A1 | 12/2007 | Lovell et al. | |
| 2008/0200344 A1 | 8/2008 | Cheng | |
| 2008/0247914 A1 | 10/2008 | Edens et al. | |
| 2009/0032445 A1 | 2/2009 | Doak et al. | |
| 2009/0263819 A1 | 10/2009 | Muraca | |
| 2009/0286687 A1 | 11/2009 | Dressman et al. | |
| 2009/0298187 A1 * | 12/2009 | Nazarenko et al. | 436/94 |
| 2010/0081124 A1 | 4/2010 | Abravaya et al. | |
| 2010/0105060 A1 | 4/2010 | Eder et al. | |
| 2010/0126286 A1 | 5/2010 | Self et al. | |
| 2010/0129789 A1 | 5/2010 | Self et al. | |
| 2010/0159463 A1 | 6/2010 | Eder et al. | |
| 2010/0311039 A1 | 12/2010 | Lowe et al. | |
| 2011/0009277 A1 | 1/2011 | Devos et al. | |
| 2014/0087449 A1 | 3/2014 | Ballhause et al. | |

FOREIGN PATENT DOCUMENTS

| | | |
|---|---|---|
| EP | 0079139 | 5/1983 |
| EP | 0 163 220 | 12/1985 |
| EP | 0 167 366 | 1/1986 |
| EP | 0184017 | 6/1986 |
| EP | 0 281 927 | 9/1988 |
| EP | 0 288 737 | 11/1988 |
| EP | 0333465 | 9/1989 |
| EP | 0 336 454 | 11/1992 |
| EP | 0 144 914 | 6/1995 |
| EP | 0 415 978 | 3/1996 |
| EP | 0 703 296 | 3/1996 |
| EP | 1 806 410 A2 | 7/2007 |
| EP | 2 184 368 A1 | 5/2010 |
| JP | T H-07-505759 A | 6/1995 |
| JP | 200400508019 A | 3/2004 |
| JP | T-2007-509861 A | 4/2007 |
| JP | 2009 106220 | 5/2009 |
| WO | 8607387 | 12/1986 |
| WO | 88/03957 | 6/1988 |
| WO | 91/08312 | 6/1991 |
| WO | 93/10263 | 5/1993 |
| WO | WO 93/10263 A1 * | 5/1993 |
| WO | 84/02721 | 7/1994 |
| WO | 94/16108 | 7/1994 |
| WO | 95/16055 | 6/1995 |
| WO | 95/17430 | 6/1995 |
| WO | 96/40992 | 5/1996 |
| WO | 96/40992 | 12/1996 |
| WO | 97/05277 | 2/1997 |
| WO | 97/10364 | 3/1997 |
| WO | 97/31256 | 8/1997 |
| WO | 98/18488 | 5/1998 |
| WO | 98/22620 | 5/1998 |
| WO | 98/59044 | 12/1998 |
| WO | 99/02488 | 1/1999 |
| WO | 99/29909 | 6/1999 |
| WO | 99/32654 | 7/1999 |
| WO | 99/36571 | 7/1999 |
| WO | 99/39001 | 8/1999 |
| WO | 99/40224 | 8/1999 |
| WO | 99/49224 | 9/1999 |
| WO | 99/50459 | 10/1999 |
| WO | 00/60116 | 10/2000 |
| WO | 01/36681 | 5/2001 |
| WO | 01/96608 A1 | 12/2001 |
| WO | 0196608 | 12/2001 |
| WO | 02066993 A1 | 8/2002 |
| WO | 2004/087950 | 10/2004 |
| WO | 2005042030 A1 | 5/2005 |
| WO | 2005/080602 | 9/2005 |
| WO | 2005/088311 A1 | 9/2005 |
| WO | 2006039563 A2 | 4/2006 |
| WO | 2006/124771 A2 | 11/2006 |
| WO | 2007/056723 | 5/2007 |
| WO | 2007/130519 A2 | 11/2007 |
| WO | 2007134252 A1 | 11/2007 |
| WO | 2008/036061 | 3/2008 |
| WO | 2008/139938 A1 | 11/2008 |
| WO | 2008149237 A2 | 12/2008 |
| WO | 2009/057993 A1 | 5/2009 |
| WO | 2009/123996 | 10/2009 |
| WO | 2010/004251 A1 | 1/2010 |
| WO | 2010/028382 | 3/2010 |
| WO | 2010/127228 A1 | 11/2010 |

OTHER PUBLICATIONS

Monteiro et al., 1997 Evaluation of Performances of Three DNA Enzyme Immunoassays for Detection of Helicobacter pylori PCR Products from Biopsy Specimens Journal of Clinical Microbiology, 35:2931-2936.

Chiu et al., 1998 "Sandwich-type Deoxyribonucleic Acid Hybridization Assays Based on Enzyme Amplified Time-Resolved Fluorometry" Analyst , 123:1315-1319.

(56) References Cited

OTHER PUBLICATIONS

White et al., 1999 "Signal Amplification System for DNA Hybridization Assays Based on in vitro Expression of a DNA Label Encoding Apoaequorin" Nucleic Acids Research 27:i-viii.
Hakala et al., 1998 "Detection of Oligonucleotide Hybridization on a Single Microparticle by Time-Resolved Fluorometry: Quantitation and Optimization of a Sandwich Type Assay" Bioconjugate Chem. 9:316-321.
Zammatteo et al., 1997 "Comparison between Microwell and Bead Supports for the Detection of Human Cytomegalovirus Amplicons by Sandwich Hybridization" Analytical Biochemistry 253:180-189.
Fisher et al., 1997 "A System for the Quantitation of DNA Using a Microtiter Plate-Based Hybridization and Enzyme Amplification Technology" Analytical Biochemistry 251:280-287.
Wicks et al., 1998 "A Sandwich Hybridization Assay Employing Enzyme Amplification for Determination of Specific Ribosomal RNA from Unpurified Cell Lysates" Analytical Biochemistry 259:258-264.
Bruckner-Lea et al., 2000 "Rotating Rod Renewable Microcolumns for Automated, Solid-Phase DNA Hybridization Studies" Anal. Chem. 72:4135-4141.
Allen et al., 1998 "High Resolution Genetic Typing of the Class II HLA-DRB 1 Locus Using Group-Specific Amplification and SSO-Hybridisation in Microplates" Hereditas 129:161-167.
Chomvarin et al., 2000 "Development of EIA for Detection of Chlamydia Trachomatis in Genital Specimens" The Southeast Asian Journal of Tropical Medicine and Public Health, 31:96-103.
Alexandre et al., 1998 "Quantitative Determination of CMV DNA Using a Combination of Competitive PCR Amplification and Sandwich Hybridization" BioTechniques, 25: 676-683.
Casademont et al., 2000 "Rapid Detection of Campylobacter fetus by Polymerase Chain Reaction Combined With Non-Radioactive Hybridization Using an Oligonucleotide Covalently Bound to Microwells" Molecular and Cellular Probes 14:233-240.
Hara et al., "Small Sample Whole-Genome Amplification," Optics East 2005, UCRL-PROC-216415, Lawrence Livermore National Laboratory, Oct. 21, 2005.
Brigotti, et al., "A rapid and sensitive method to measure the enzymatic activity of ribosome-inactivating proteins," Nucleic Acids Res., vol. 26, No. 18, pp. 4306-4307, 1998.
PCT/US2009/062061, International Searching Authority, Oct. 26, 2009 (6 pages).
PCT/US2009/062041, International Searching Authority, Oct. 26, 2009 (5 pages).
U.S. Appl. No. 12/622,131, titled "Multiple-Input Analytical System," filed Nov. 19, 2009 (not yet published).
Bhan et al., "2',5'-Linked oligo-3'-deoxyribonucleoside phosphorothioate chimeras: thermal stability and antisense inhibition of gene expression," Nucleic Acids Research, 1997, vol. 25, No. 16, pp. 3310-3317 (XP-002560367).
Genetech Diagnostics Pvt. Ltd., "Digene HBV Test Hybrid Capture II," Jun. 6, 2008 (XP-002560368).
Hantz et al., "Evaluation of accuracy of three assays for human papillomavirus detection and typing: Hybrid Capture 2, HPV Consensus kit and Amplicor HPV," Pathologie Biologie, Feb. 2008, vol. 56, No. 1, pp. 29-35 (XP002560369).
Sandri et al., "Comparison of the Digene HC2 Assay and the Roche AMPLICOR Human Papillomavirus (HPV) Test for Detection of High-Risk HPV Genotypes in Cervical Samples," Journal of Clinical Microbiology, Jun. 2006, vol. 44, No. 6, pp. 2141-2146 (XP002560370).
Boston Bioproducts Inc., "Protein Extraction buffers," Sep. 2, 2007 (XP002560371).
Bart "General Principles of Immunoprecipitation," Jul. 31, 2008 (XP002560372).
Mittendorf T, et al., "HPV-DNA-Diagnostik zur Zervixkarzinomfrüherkennung; Deutsche Agentur für HTA des Deutschen Instituts für Medizinische Dokumentation und Information," 1. Auflage 2007.
Nanda K, et al., "Accuracy of the Papanicolaou Test in Screening for and Follow-up of Cervical Cytologic Abnormalities: A Systematic Review, Annals of Internal Medicine," 132(10)810-819, May 16, 2000.
Davey DD, et al., "Introduction and Commentary, Strategic Science Symposium, Human Papillomavirus Testing—Are you ready for a new era in cervical cancer screening?," Arch Pathol Lab Med, 127: 927-929, Aug. 2003.
Malloy C, et al., "HPV DNA Testing: Technical and Programmatic Issues for Cervical Cancer Prevention in Low-Resource Settings," Path, Dec. 2000.
Stacey SN, et al., "Translation of the Human Papillomavirus Type 16 E7 Oncoprotein from Bicistronic mRNA is independent of Splicing Events within the E6 Open Reading Frame," Journal of Virology. 69(11):7023-7031. Nov. 1995.
Hsu E, et al., Quantification of HPV-16 E6-E7 Transcription in Cervical Intraepithelial Neoplasia by Reverse Transcriptase Polymerase Chain Reaction, Int. J. Cancer: 55, 397-401 (1993).
Bohm S, et al., "The Predominant mRNA Class in HPV16-Infected Genital Neoplasias does not Encode the E6 or the E7 Protein," Int. J. Cancer: 55, 791-798 (1993).
Middleton, K, et al., "Organization of Human Papillomavirus Productive Cycle during Neoplastic Progression Provides a Basis for Selection of Diagnostic markers." Journal of Virology. Oct. 2003. pp. 10186-10201.
Stoler, M, et al., "Human Papillomavirus Type 16 and 18 Gene Expression in Cervical Neoplasias," Human Pathol. 23 (1992), pp. 117-128.
Higgins, G, et al., "Transcription patterns of human papillomavirus type 16 in genital intraepithelial neoplasia: evidence for promoter usage within the E7 open reading frame during epithelial differentiation," J. Gen. Virol. 73(1992), pp. 2047-2057.
Karlsen, F, et al., "Use of Multiple PCR Primer Sets Optimal Detection of Human Papillomavirus," J. Clin. Microbiol. 34 (1996), pp. 2095-2100.
Park, JS, et al., "Physical Status and Expression of HPV Genes in Cervical Cancers," Gynec. Oncol. 95 (1997), pp. 121-129.
Broker, TR, et al., "A Molecular Portrait of Human Papillomavirus Carcinogenesis," Cancer Cells 7 (1989), pp. 197-207.
Letter dated Jan. 6, 2010 to EPO re EP 1 038 022 (46 pages).
Letter to EPO dated Mar. 2, 2009 re EP 1 038 022 (15 pages).
Letter to EPO dated Oct. 6, 2008 re EP 1 038 022 (27 pages).
Letter to EPO dated Aug. 8, 2008 re EP 1 038 022 (11 pages).
EPO decision dated May 27, 2008 re Opposition of EP 1 038 022 (19 pages).
Letter to EPO dated Jan. 25, 2008 re EP 1 038 022 (10 pages).
Letter to EPO dated Jan. 23, 2008 re EP 1 038 022 (6 pages).
Communication from EPO dated May 14, 2007 re EP 1 038 022 (8 pages).
Letter to EPO dated Oct. 4, 2006 re EP 1 038 022 (11 pages).
Letter to EPO dated Apr. 18, 2006 re EP 1 038 022 (10 pages).
Partial International Search Report for PCT/US2009/062041, mail date Jan. 5, 2010.
Partial International Search Report for PCT/US2009/062041, mail date Apr. 8, 2010.
Thai et al., "An HPV 16, 18, and 45 genotyping test based on Hybrid Capture technology," Journal of Clinical Virology 45, S1 (2009) pp. 593-597.
Kitagawa et al., "Comparison of Poly(A) Poly(dT) and Poly(I) Poly (dC) As Immunogens for the Induction of Antibodies to RNA-DNA Hybrids," Molecular Immunology, vol. 19, No. 3, pp. 413-420, 1982.
Ishikawa et al., "Enzyme-Labeling of Antiboldies and Their Fragments for Enzyme Immunoassay and Immunohistochemical Staining," Journal of Immunoassay and Immunochemistry, 4: 3, 209-327.
Means et al., "Chemical Modifications of Proteins: History and Applications," Bioconjugate Chem. 1990, 1, 2-12.
Jakobovits et al., "Analysis of homozygous mutant chimeric mice: Deletion of the immunoglobulin heavy-chain joining region blocks B-cell development and antibody production," Proc. Natl. Acad. Sci. USA, vol. 90, pp. 2551-2555, Mar. 1993 Genetics.

(56) References Cited

OTHER PUBLICATIONS

Jakobovits et al., "Germ-line transmission and expression of a human-derived yeast artificial chromosome," pp. 255-258, Nature, vol. 362, Mar. 18, 1993.
International Search Report for PCT/US2009/041033, dated Dec. 22, 2009.
Sigurdsson et al., "Human papillomavirus (HPV) in an icelandic population: the role of HPV DNA testing based on hybrid capture and PCR assays among women with screen-dtected abnormal PAP smears," In: International Journal of Cancer, Jul. 1997, vol. 72(3), pp. 446-452.
Michele De Villiers et al., "Classification of papillomarviruses," In: Virology, Jun. 2004, vol. 324(1), pp. 17-27—see table 3.
GenBank Accession No. K02718, "Human papillomavirus type 16 (HPV16), complete genome.", Mar. 18, 1994. See http://www.ncbi.nlm.nihgov/nuccore/333031.
GenBank Accession No. X74479, "Human papillomavirus type 45 genomic DNA.", Apr. 18, 2005. See http://www.ncbi.nlm.nih.gov/nuccore/397022.
GenBank Accession No. X05015, "Human papillomavirus type 18 E6, E7, E1, E2, E4, E5, L1 & L2 genes.", Apr. 18, 2005. See http://www.ncbi.nlm.nih.gov/nuccore 60975.
GenBank Accession No. J04353, "Human papillomavirus type 31 (HPV-31), complete genome.", Mar. 18, 1994. See http://www.ncbi.nlm.nih.gov/nuccore/333048.
GenBank Accession No. M12732, "Human papillomavirus type 33, complete genome.", Mar. 21, 1994. See http://www.ncbi.nlm.nih.gov/nuccore/333049.
GenBank Accession No. M74117, "Human papillomavirus type 35, complete genome.", May 10, 2002. See http://www.ncbi.nlm.nih.gov/nuccore/333050.
GenBank Accession No. M62849, "Human papillomavirus ORFs.", Jan. 26, 2001. See http://www.ncbi.nlm.nih.gov/nuccore/333245.
GenBank Accession No. M62877, "Human papillomavirus type 51 genomic DNA, partial sequence.", Oct. 29, 1999. See http://www.ncbi.nlm.nih.gov/nuccore/333087.
GenBank Accession No. X74481, "Human papillomavirus type 52 genomic DNA.", Apr. 18, 2005. See http://www.ncbi.nlm.nih.gov/nuccore/397038.
GenBank Accession No. X74483, "Human papillomavirus type 56 genomic DNA.", Apr. 18, 2005. See http://www.ncbi.nlm.nih.gov/nuccore/397053.
GenBank Accession No. D90400, "Human papillomavirus type 58, complete genome.", Dec. 7, 2007. See http://www.ncbi.nlm.nih.gov/nuccore/222386.
GenBank Accession No. X77858, "Human papillomavirus type 59, complete viral genome.", Apr. 18, 2005. See http://www.ncbi.nlm.nih.gov/nuccore/557236.
GenBank Accession No. U31794, "Human papillomavirus type 66, complete genome.", Oct. 18, 1995. See http://www.ncbi.nlm.nih.gov/nuccore/1020290.
GenBank Accession No. X67161, "Human papillomavirus type L1 gene for major capsid protein.", Apr. 18, 2005. See http://www.ncbi.nlm.nih.gov/nuccore/1197494.
GenBank Accession No. AB027021 , "Human papillomavirus type 82 DNA, complete genome.", Jun. 22, 2000. See http://www.ncbi.nlm.nih.gov/nuccore/6970427.
Kleter et al., "Development and clinical evaluation of a highly sensitive PCT-reverse hybridization line probe assay for detection and identification of anogenital human papillomafirus," In: Journal of clinical Micorbiology, Aug. 1999, vol. 37(8), pp. 2508-2517, see the whole document.
Supplementary European Search Report of PCT/US2006/060603, dated Jul. 7, 2010 (8 pages).
Lowe, et al., "A computer program for selection of oligonucleotide primers for polymerase chain reactions", Nucleic Acid Res., vol. 18, No. 7, pp. 1757-1761 (1990).
International Search Report and Written Opinion of PCT/US2010/022264 dated Jun. 7, 2010 (19 pages).

Cohenford at al., "C-195. Rapid Detection of Chlamydia trachomatis from Specimens Collected from the ThinPrep Pap Test using Molecular Beacons and the Roche LightCycler," Abstracts of the General Meeting of the American Society for Microbiology, The Society, Washington, DC. (Jan. 1, 2001), p. 195, vol. 101, XP001098006.
Gentech Diagnostics: "Chlamydia DNA Test Kit," (Jun. 6, 2008), XP002578832, Retrieved from the Internet: URL: http://www.gentechin.com/chlamydiatestkit.htm.
Taha et al., "Universal Collection Medium (UCM) is as suitable as the Standard Transport Medium (STM) for Hybrid Capture II (HC-2) assay," Journal of Clinical Virology, (May 1, 2006), pp. 32-35, vol. 36, No. 1. XP005367693.
Darwin et al., "Comparison of Digene Hybrid Capture 2 and Conventional Culture for Detection of Chlamydia trachomatis and Neisseria gonorrhoeae in Cervical Specimens," Journal of Clinical Microbiology, (Feb. 2002), pp. 641-644, vol. 40, No. 2, XP002578833.
Nazarenko et al., "A novel method of HPV genotyping using Hybrid Capture sample preparation method combined with GP5+/6+ PCR and multiplex detection on Luminex XMAP," Journal of Clinical Virology, (Dec. 1, 2008), pp. 76-81, vol. 154, No. 1-2, XP025680302.
International Search Report and Written Opinion of PCT/US10/33145, dated Aug. 5, 2010 (9 pages).
A Lorincz, "Hybrid Capture," Clin. Chem., (Jun. 1998), pp. 1363, vol. 44, No. 6 (Note that the page number of this literature listed on the ISR is incorrect).
Vernick et el., "The HPV DNA virus hybrid capture assay: What is it—and where do we go from here?" MLO Med. Lab. Obs., (Mar. 2003), pp. 8-10, 13, vol. 35, No. 3.
International Search Report and Written Opinion of PCT/US2010/048714, dated Dec. 10, 2010 (14 pages).
International Preliminary Report on Patentability and Written Opinion of PCT/US2009/041033, dated Oct. 19, 2010 (6 pages).
International Search Report and Written Opinion of PCT/US2010/047769, dated Nov. 9. 2010 (11 pages).
Pachowics, et al., "Sequence specific large volume sample prep solution utilizing Hybrid Capture technology," 41st Annual Oak Ridge Conference; Baltimore, MD; Apr. 16, 2009, retrieved from the Internet: http://www.aacc.org/events/meeting_proceeding/2009/Documents/OakRidge09AllPosters.pdf.
Keegan et al., "Comparison of HPV detection technologies: Hybrid capture 2, PreTect HPV-Proofer and analysis of HPV DNA viral load in HPV16, HPV18 and HPV33 E6/E7 mRNA positive specimens," Journal of Virological Methods, Jan. 1, 2009, pp. 61-66, vol. 155, No. 1, Elsevier BV, XP025799776.
Murphy et al., "Isolation of RNA from cell lines and cervical cytology specimens stored in BD SurePath (TM) preservative fluid and downstream detection of housekeeping gene and HPV E6 expression using real time RT-PCR," Journal of Virological Methods, Mar. 1, 2009, pp. 138-144, vol. 156, No. 1-2, Elsevier BV, XP025941323.
Powell et al., "Recovery of human papillomavirus nucleic acids from liquid-based cytology media," Journal of Virological Methods, Oct. 1, 2006, pp. 58-62, vol. 137, No. 1, Elsevier BV, XP005600251.
Nindl et al., "Human Papillomavirus Distribution in Cervical Tissues of Different Morphology as Determined by Hybrid Capture Assay and PCR," International Journal of Gynecological Pathology, Jan. 1, 1997, pp. 197-204, vol. 16, No. 3, Lippincott-Raven Publishers, XP008011933.
Hernandez-Hernandez et al., "Association between high-risk human papillomavirus DNA load and precursor lesions of cervical cancer in Mexican women," Gynecologic Oncology, Aug. 2003, pp. 310-317, vol. 90, No. 2, Elsevier Science, XP002603500.
Tsai et al., "Association between Quantitative High-Risk Human Papillomavirus DNA Load and Cervical Intraepithelial Neoplasm Risk," Cancer Epidemiology, Biomarkers & Prevention: American Association for Cancer Research, Nov. 2005, pp. 2544-2549, vol. 14, No. 11 pt 1, XP002603501.

(56) References Cited

OTHER PUBLICATIONS

Moodley et al., "Human papillomavirus prevalence, viral load and pre-cancerous lesions of the cervix in women initiating highly active antiretroviral therapy in South Africa: a cross-sectional study," BMC Cancer, Aug. 7, 2009, pp. 1-8, vol. 9, No. 275, Biomed Central Ltd, XP002603502.

Ronco et al., "HPV triage for low grade (L-SIL) cytology is appropriate for women over 35 in mass cervical cancer screening using liquid based cytology," European Journal of Cancer, Feb. 1, 2007, pp. 476-480, vol. 43, No. 3, Pergamon Press, Oxford GB, XP005868775.

Larder et al. "Related Functional Domains in Virus DNA Polymerases," The EMBO Journal. vol. 6, No. 1, pp. 160-175, 1987.

Lowe et al., "HPV Genotype Detection Using Hybrid Capture Sample Preparation Combined with Whole Genome Amplification and Multiplex Detection with Luminex XMAP," Journal of Molecular Diagnostics; Nov. 6, 2010; pp. 847-853; vol. 12; No. 6; American Society for Investigative Pathology.

Partial European Search Report of EP10185824; mailed Feb. 16, 2011 (8 pages).

Scott et al., "Detection of herpes simplex virus type 1 shedding in the oral cavity by polymerase chain reaction and enzyme-linked immunosorbent assay at the prodromal stage of recrudescent herpes labialis," Journal of Oral Pathology & Medicine; Aug. 1997; pp. 305-309; vol. 26; No. 7; XP009143938.

Ryncarz et al., "Development of a High-Throughput Quantitative Assay for Detecting Herpes Simplex Virus DNA in Clinical Samples," Journal of Clinical Microbiology; Jun. 1999; pp. 1941-1947; vol. 37, No. 6; American Society for Microbiology.

Yevgeniy S Belousov et al.: "Single nucleotide polymorphism genotyping by two colour melting curve analysis using the MGB elicpse TM probe system in challenging sequence environment" Human Genomics, Henry Stewart Publications, London, GB, vol. 1, No. 3, Jan. 1, 2004, pp. 209-217; XP001538494.

International Search Report and Written Opinion based on PCT/US2001/037012 mailed Apr. 17, 2012.

Chinese First Action dated Aug. 2, 2013, issued in Application No. 201180016276.3 and English translation thereof.

Molijn A. et al., "Molecular diagnosis of human papillomavirus (HPV) infections," Journal of Clinical Virology, 2005, vol. 32S at pp. S43-S51.

Lowe et al.; "A Hybrid-Capture Assay to Detect HPV MRNA Ratios in Cervical Specimens"; Journal of Virological Methods; vol. 179; No. 1; Jan. 2012; pp. 142-147.

International Search Report Based on Application No. PCT/US2012/026380 mailed Oct. 15, 2012.

International Search Report Based on Application No. PCT/US2012/020684 mailed Oct. 25, 2012.

Clad et al.; "Performance of the Aptima High-Risk Human Papillomavirus MRNA Assay in a Referral Population in Comparison With Hybrid Capture 2 and Cytology"; Journal of Clinical Microbiology; Mar. 2011; LNKD-PUBMED:21191046; vol. 49; No. 3; Dec. 29, 2010; pp. 1071-1076; Abstract.

Li et al; Detection of Human Papillomavirus Genotypes With Liquid Bead Microarray in Cervical Lesions of Northern Chinese Patients; Cancer Genetics and Cytogenetics, Elsevier Science Publishing, New York, NY, US; vol. 182; No. 1; Mar. 6, 2008; pp. 12-17; Abstract.

Gheit et al.; "Development of a Sensitive and Specific Assay Combining Multiplex PCR and DNA Microarray Primer Extension to Detect High-Risk Mucosal Human Papillomavirus Types"; Journal of Clinical Microbiology, American Society for Microbiology, Washington, DC, US; vol. 44; No. 6; Jun. 1, 2006; pp. 2025-2031; Abstract.

Han et al.; "Simultaneous Amplification and Identification of 25 Human Papillomavirus Types With Templex Technology"; Journal of Clinical Microbiology 200611 US LNKD-DOI:10.1128/JCM. 01762-06; vol. 44; No. 11; Nov. 2006; pp. 4157-4162; Abstract.

Database EMBL [Online]; Jul. 19, 2007; "Sequence 25 From Patent EP1806410"; XP002675256; Retrieved From EBI Acession No. EMBL:CS642417; Database Accession No. CS642417; the Whole Document.

Database EMBL [Online]; Dec. 14, 2010; "Sequence 26 From U.S. Pat. No. 7,812,144"; XP00267527; Retrieved from EBI Accession No. EMBL:GX640151; Database Accession No. GX640151; the Whole Document.

Database Geneseq [Online]; Jan. 22, 2009; "HPV-16 E7/E6 Gene Target Sequence, Bases 752-774"; XP002675258, Retrieved from EBI Accession No. GSN:ATS82292; Database Accession No. ATS82292; the Whole Document.

Database Geneseq [Online]; Jan. 22, 2009; "HPV-16 E7/E6 Gene Target Sequence, Bases 698-720"; XP002675259 Retrieved From EBI Accession No. GSN:ATS82290; Database Accession No. ATS82290; the Whole Document.

Database Geneseq [Online]; Apr. 1, 2010; "HPV16 E7 Gene Forward RT-PCR Primer SEQ ID 49"; XP002675260; Retrieved From EBI Accession No. GSN:AXU96631; Database Accession No. AXU96631; the Whole Document.

Database Geneseq [Online]; Apr. 21, 2005; "E7 Coding Region (1-87) Amplifying Sense PCR Primer, SEQ ID No. 37"; XP002675261; Retrieved From EBI Accession No. GSN:ADX15568; Database Accession No. ADX15568; Sequence.

Broker et al., "A Molecular Portrait of Human Papillomavirus Carcinogenesis", Cancer Cells, vol. 7, pp. 197-208, 1989 (Roche EU Opposition).

Higgins et al., "Transcription Patterns of Human Papillomavirus Type 16 in Genital Intraepithelial Neoplasia: Evidence for Promoter Usage within the E7 Open Reading Frame during Epithelial Differentiation", Journal of General Virology, vol. 73, pp. 2047-2057, 1992 (Roche EU Opposition).

Karlsen et al., "Use of Multiple PCR Primer Sets for Optimal Detection of Human Papillomavirus", Journal of Clinical Microbiology, pp. 2095-2100, Sep. 1996 (Roche EU Opposition).

Park et al., "Physical Status and Expression of HPV Genes in Cervical Cancers", Gynecologic Oncology, vol. 65, pp. 121-129, 1997 (Roche EU Opposition).

Stoler et al., "Human Papillomavirus Type 16 and 18 Gene Expression in Cervical Neoplasias", Human Pathology, vol. 23, No. 2, pp. 117-128, Feb. 1992 (Roche EU Opposition).

De Villiers et al., "Classification of Papillomaviruses", Virology, vol. 324, pp. 17-27, 2004.

Howley et al., "A Rapid Method for Detecting and Mapping Homology between Heterologous DNAs", Journal of Biological Chemisny, vol. 254, No. 11, pp. 4879-4883, Jun. 10, 1979.

Law et al., "Conserved Polynucleotide Sequences Among the Genomics of Papillomaviruses", Journal of Virology, vol. 32, No. 1, pp. 199-207, Oct. 1979.

Heilman et al., "Cloning of Human Papilloma Virus Genomic DNAs and Analysis of Homologous Polynucleotide Sequences", Journal of Virology, vol. 36, No. 2, pp. 395-407, Nov. 1980.

Howard et al., "Optimizing the Hybrid Capture II Human Papillomavirus Test to Detect Cervical Intraepithelial Neoplasia", Obstetrics and Gynecology, vol. 100, No. 5, Part 1, pp. 972-980, Nov. 2002.

Lorincz, A.T., "Molecular Methods for the Detection of Human Papillomavirus Infection", Obstetrics and Gynecology Clinics of North America, vol. 23, No. 3, pp. 707-730, Sep. 1996.

B.D. Hames, et al., "Nucleic Acid Hybridization. A Practical Approach." 1985.

Greg T. Hermanson et al., "Immobilized Affinity Ligand Techniques." 1992.

Richard F. Taylor, "Protein Immobilization. Fundamentals and Applications." 1991.

Blair et al. "Herpes Simplex Virus Viron Stimulatory Protein mRNA Leader Contains Sequence Elements Which Increase Both Virus-Induced Transcription and tnRNA Stability." Journal of Virology, vol. 61, No. 8, pp. 2499-2508, Aug. 1987.

Brendan et al. "Related Functional Domains in Virus DNA Polymerases," The EMBO Journal. vol. 6, No. 1, pp. 160-175, 1987.

(56) References Cited

OTHER PUBLICATIONS

Chandler et al., Detection of Dengue-2 Viral RNA by Reversible Target Capture Flybridization., J. Clin. Microbiol., vol. 31 (10), pp. 2641-2647, 1993.
Mazzulli et al, 1999, Multicenter Comparison of the Digene Hybrid Capture CMV DNA Assay (version 2.0) the pp65 Antignenemia Assay, and Cell Culture for Detection of Cytomegalovirus Viremia, J Clin. Microbiol., vol. 37, No. 4, pp. 958-963, 1999.
Murakami et al., Fluorescent-Labeled Oligonucleotide Probes: Detection of Hybrid Formation in Solution by Fluorscence Polarization Spectroscopy, Nucleic Acids Res., vol. 19 (15), pp. 4097-4102, 1991.
Dunn and Hassell: "A Novel Method to Map Transcripts: Evidence for Homology between an Adenovirus niRNA and Discrete Multiple Regions of the Viral Genome" Cell, 12:23-36, Sep. 1977.
Coutlee et al., "Nonisotopic Detection of RNA in an Enzyme Imunoassay using a Monoclonal Antibody Against DNA-RNA Hybrids" Analytical Biochemistry 181:153-162, 1969.
Chen et al., "DNA Optical Sensor: A Rapid Method for the Detection of DNA Hybridization" Biosensors & Bioelectronics 13:451-458, 1998.
Chevrier et al., "Isolation of a Specific DNA fragment and Development of a PCR Based Method for the Detection of Mycobacterium genavense" FEMS Immunology and Medical Microbiology 23:243-452, 1999.
Hakala et al., "Simultaneous Detection of Several Oligonucleotides by Time-Resolved Fluorometry: The Use of a Mixture of Categorized Microparticles in a Sandwich Type Mixed-Phase Hybridization Assay" Nucleic Acid Research, 26:5581-5588, 1998.
Gelmetti et al., "Detection of Rabbit Haemorrhagic Disease Virus (RHDV) by in Situ Hybridisation With a Digoxigenin Labelled RNA Probe" Journal of Virological Methods 72:219-226, 1998.
Radtkey et al., "Rapid, High Fidelity Analysis of Simple Sequence Repeats on an Electronically Active DNA Microchip" Nucleic Acids Research 28:i-vi, 2000.
Namimatsu et al., "Detection of Salmonella by Using the Colorimetric DNA/rRNA Sandwich Hybridization in Microtiter Wells" J. Vet. Med. Sci. 62:615-619, 2000.
Lazar et al., 1999 "Hybrid Capture®: a Sensitive Signal Amplification-based Chemiluminescent Test for the Detection and Quantitation of Human Viral and Bacterial Pathogens".1. Clin. Ligand Assay 22:139-151.
Newman et al., 1989 "Solution Hybridization and Enzyme Immunoassay for Biotinylated DNA:RNA Hybrids to Detect Enteroviral RNA in Cell Culture" Mol. Cell Probes 3:375-382.
Lamoureux et al., 1997 "Detection of Campylobacter jejuni in Food and Poultry Viscera Using Immunomagnetic Separation and Microtitre Hybridization" J. Appl. Microbiol. 83:641-651.
Coutlee et al., 1990 "Quantitative Detection of Messenger RNA by Solution Hybridization and Enzyme Immunoassay" Biol. Chem. 265:11601-11604.
Stollar, B.D. and A. Rashtchian, 1987 "Immunochemical Approaches to Gene Probe Assays" Anal. Biochem. 161:387-394.
Blais, B.W., 1994 "Transcriptional Enhancement of the Listeria Monocytogenes PCR and Simple Immunoenzymatic Assay of the Product Using Anti-RNA:DNA Antibodies" AppL Environ Microbiol. 60:348-352.
Coutlee et al., 1991 "Detection of Transcripts of Human Papillomaviruses 16 and 18 in Cancer-derived Cell Lines and Cervical Biopsies by Enzyme Immunoassay for DNA-RNA Hybrids Following Solution Hybridization" J. Clin. Microbiol. 29:968-974.
Viscidi et al., 1989 "Monoclonal Antibody Solution Hybridization Assay for Detection of Human Immunodeficiency Virus Nucleic Acids" J. Clin. Microbiol. 27:120-125.
Boguslawski et al., 1986 "Characterization of Monoclonal Antibody to DNA:RNA and Its Application to Immunodetection of Hybrids" J. Immunol. Methods 89:123-130.
Coutlee et al., 1989 "Immunodetection of DNA with Biotinylated RNA Probes: A Study of Reactivity of a Monoclonal Antibody to DNA-RNA Hybrids" Anal. Biochem. 181:96-105.
Coutlee et al., 1991 "Immunodetection of DNA with Biotinylated RNA Probes: A Study of Reactivity of a Monoclonal Antibody to DNA-RNA Hybrids" Anal. Biochem. 198:217 (Published erratum).
Coutlee et al., 1989 "Comparison of Colorimetric Fluorescent, and Enzymatic Amplification Substrate Systems in an Enzyme Immunoassay for Detection of DNA-RNA Hybrids" J. Clin. Microbiol. 27:1002-1007.
Dalrymple et al., DNA sequence of the herpes simplex virus type 1 gene whose product is responsible for transcriptional activation of immediate early promoters, Nucleic Acids Research, 1985, vol. 13, No. 21, pp. 7865-7879.
McLauchlan et al., DNA sequence homology between two co-linear loci on the HSV genome which have different transforming abilities, The EMBO Journal, 1983, vol. 2, No. 11, pp, 1953-1961.
Goldsborough et al., Nucleotide Sequence of Human Papillomavirus Type 31: A Cervical Neoplasia Associated Virus, Virology, 1989, vol. 171, pp. 306-311.
McGeoch et al., "DNA Sequence and Genetic Content of the HindIII 1 Region in the Short Unique Component of the Herpes Simplex Virus Type 2 Genome; Identification of the Gene Encoding Glycoprotein G, and Evolutionary Comparisons," J. Gen. Virol., 1987, vol. 68, pp. 19-38.
McGeoch et al., The Complete DNA Sequence of the Long Unique Region in the Genome of Herpes Simplex Virus Type I, 1 Gen Virol., 1988, vol. 69, pp. 1531-1574.
Yamada et al., Human Papillomavirus Type 16 Variant Lineages in United States Populations Characterized by Nucleotide Sequence Analysis of the E6, L2, and LI Coding Segments, J. Virol., Dec. 1995, vol. 69, No. 12, pp. 7743-7753.
Swain et al., Nucleotide Sequence of the Herpes Simplex Virus Type 2 Thymidine Kinase Gene, Virol., Jun. 1983, vol. 46, No. 3, pp. 1045-1050.
Delius et al., Primer-Directed Sequencing of Human Papillomavirus Types, Current Topics in Microbiology and Immunology, 1994, vol. 185, pp. 13-31.
Blair et al., Herpes Simplex Virus Virion Stimulatory Protein mRNA Leader Contains Sequence Elements Which Increase Both Virus-Induced Transcription and mRNA Stability, J Virol., Aug. 1987, vol. 62, No. 2, pp. 444-453.
Larder et al., Related functional domains in virus DNA polymerases, The EMBO J., 1987, vol. 6, No. 1, pp. 169-175.
McGeoch et al., Structures of Herpes Simplex Virus Type 1 Genes Required for Replication of Virus DNA, J. Virol., vol. 62, No. 2, pp. 444-453.
Luo et al., "Adiponectin stimulates human osteoblasts proliferation and differentiation via the MAPK signaling pathway," Experimental Cell Research, Academic Press, US, 309: 1, (Sep. 10, 2005) 99-109, XP005037411.
Ouitas N. et al., "A Novel ex vivo skin model for the assessment of the potential transcutaneous anti-inflammatory effect of topically applied Harpagophytum procumbens extract," International Journal of Pharmaceutics, Elsevier BV, NL, 376: 1-2, (Jul. 6, 2009), 63-68, XP026185227.
Scholz et al., "Analysis of human immunodeficieny virus matrix domain replacements," Virology, Elsevier, Amsterdam, NL. 371: 2, (Nov. 8, 2007) 322-335, XP022439785.
Xie H. et al., "Apelin in and its receptor are expressed in human obsteoblasts," Regulatory Peptides, Elsevier Science B.V., NL, 134: 2-3, (May 15, 2006), 118-125, XP27895144.
Zhang W. et al., "Bone-Targeted Overespression of Bcl-2 Increases Osteoblast Adhesion and Differentiation and Inhibits of Mineralization In Vitro," Calcified Tissue International, Springer-Verlag, NE, 80: 2, (Feb. 2, 2007), 111-122.
European Office Action dated Jul. 14, 2014, issued in Application No. 10 755 291.1-1406.
European Office Action dated Jul. 4, 2014, issued in Application No. 09 752 940.8-1403.
Japanese Office Action dated Jun. 30, 2014, issued in Application No. 2011-548258.
Chinese Office Action dated May 4, 2014, issued in Application No. 200980143682.9, English translation.
International Search Report and Written Opinion of PCT/US2011/22887, dated Jun. 1, 2011.

(56) References Cited

OTHER PUBLICATIONS

International Preliminary Report on Patentability and Written Opinion of PCT/US2009/062061, dated May 12, 2011.
International Preliminary Report on Patentability and Written Opinion of PCT/US2009/062041, dated May 12, 2011.
GenBank Submission FJ429103. 2009 [Retrieved from the Internet May 20, 2011: <URL:http://www.ncbl.nlm.nih.gov/nuccore/FJ429103.1>]; in entirety.
Japanese Notice of Reasons for Rejection dated Aug. 28, 2014, issued in Application No. 2012-508768.
Coutlee et al., "Nonisotopic Detection of RNA in an Enzyme Immunoassay Using a Monoclonal Antibody against DNA-RNA Hybrids." Analytical Biochemistry 181, 153-162 (1989).

\* cited by examiner

METHOD OF DETERMINING AND CONFIRMING THE PRESENCE OF AN HPV IN A SAMPLE

REFERENCE TO RELATED APPLICATIONS

This application claims priority to U.S. Provisional Patent Application No. 61/299,729, filed on Jan. 29, 2010, which is incorporated herein by reference in its entirety.

FIELD OF THE INVENTION

The present disclosure relates to methods and compositions for determining and confirming the presence of a target nucleic acid in a sample and genotyping the target nucleic acid.

BACKGROUND

Preservation of biological samples, especially clinical samples, is necessary in order to ensure continued use of the sample for various levels of analysis. Oftentimes, an investigator or physician will want to run multiple tests on a single sample so that results in one test may be correlated with the others. Moreover, where clinical samples are difficult, uncomfortable, or painful to obtain, it is preferred to not have to do so on multiple occasions for the same subject or patient. As such, a need exists to minimize the amount of sample used in certain tests so as to maximize the number of tests that may be performed on a single sample.

As just one example, cervical samples are commonly collected during gynecological examinations. Where abnormal cytological examinations of such samples are observed, it is often beneficial to determine whether the tissue is infected with a human papillomavirus (HPV) associated with cervical cancer. The most commonly used tests for HPV infection typically only distinguish between high-risk and low-risk HPV infections, but cannot distinguish between various species of high-risk or low-risk HPVs. In some circumstance, it may be useful to determine the specific genotype of HPV infection.

The digene HPV Genotyping PS™ Test (PS test) was developed for the specific detection of HPV 16, 18, and 45 and is intended to be utilized as a reflex genotyping test for samples qualitatively determined to contain a high-risk human papillomavirus (HR-HPV). The PS™ test often is used to genotype HR-HPV-positive samples identified by the digene HC2™ HPV test (HC2™ test), which is described in U.S. Pat. Nos. 4,849,331; 4,849,332; 4,849, 334; 4,908,306; 5,411,857; 5,643,715; 5,712,092; 5,876, 922; 5,952,487; 5,958,674; 6,107,086; and 5,981,173, each of which is herein incorporated by reference. Both the PS™ test and the HC2™ test are based on hybrid capture technology, which is described in, among other references, U.S. Pat. Nos. 4,732,847; 4,865,980; and 6,228,578 B1, each of which is herein incorporated by reference. The PS™ test has been demonstrated to be compatible with SPECIMEN TRANSPORT MEDIUM™ (STM) media and the commonly used liquid based cytology (LBC) media, PRESERV-CYT® (PC). However, it has not been tested with another frequently used LBC media, SUREPATH®. In addition, the intended use of the PS™ Test is to detect HPV genotypes separately, which requires separate aliquots of each patient specimen for each genotype tested. In addition, some specimens may lack sufficient volume after qualitative testing for performing separate tests for each genotype to be evaluated.

Accordingly, it would be beneficial to develop materials and methods for performing the PS™ test in SP samples and with reduced volume.

SUMMARY

The present disclosure in aspects and embodiments addresses these various needs and problems by providing a method of genotyping an target nucleic acid in a sample.

In an aspect, a method for genotyping a target nucleic acid in a sample is provided comprising:
(a) generating a first detection mixture by a method comprising contacting a portion of the sample with a first probe set, wherein the first probe set comprises a nucleic acid probe specific for a first genotype of the target nucleic acid and a nucleic acid probe specific for a second genotype of the target nucleic acid, but does not comprise a nucleic acid probe specific for a third genotype of the target nucleic acid;
(b) generating a second detection mixture by a method comprising contacting a portion of the sample with a second probe set, wherein the second probe set comprises a nucleic acid probe specific for the second genotype of the target nucleic acid and a nucleic acid probe specific for the third genotype of the target nucleic acid, but does not comprise a nucleic acid probe specific for the first genotype of the target nucleic acid; and
(c) treating the first and second detection mixtures under conditions wherein the nucleic acid probes hybridize specifically to the first, second, and/or third genotype of the target nucleic acid; and
(d) detecting hybridization of the nucleic acid probe to the target nucleic acid, wherein:
(i) hybridization in the first detection mixture, but not the second detection mixture indicates that the sample comprises the first genotype of the target nucleic acid;
(ii) hybridization in the second detection mixture, but not the first detection mixture, indicates that the sample comprises the third genotype of the target nucleic acid; and
(iii) hybridization in the first detection mixture and the second detection mixture indicates that the sample comprises the second genotype of the target nucleic acid.

In an aspect, the target nucleic acid is an HPV nucleic acid.

In an aspect, the first, second, and third genotypes of the target nucleic acid are selected from the group consisting of HPV2, HPV3, HPV6, HPV10, HPV11, HPV16, HPV18, HPV26, HPV27, HPV28, HPV29, HPV30, HPV31, HPV32, HPV33, HPV34, HPV35, HPV39, HPV42, HPV45, HPV51, HPV52, HPV53, HPV54, HPV56, HPV57, HPV58, HPV59, HPV64, HPV66, HPV67, HPV68, HPV69, HPV70, HPV73, HPV82, HPV84, HPV85, HPV86, HPV87, and HPV94 nucleic acids.

In an aspect, the first, second, and third genotypes of the target nucleic acid are HPV16, HPV18, and HPV45 nucleic acids.

In an aspect, the sample is a clinical sample preserved in a liquid based cytology medium.

In an aspect, the liquid based cytology medium is selected from the group consisting of Preservcyt and SurePath.

In an aspect, hybridization of the nucleic acid probe forms a DNA:RNA hybrid.

In an aspect, the DNA:RNA hybrid is detected by a method comprising contacting the DNA:RNA hybrid with a DNA:RNA-specific antibody.

In an aspect, the target nucleic acid is first identified as being the first, second, or third genotypes of the target nucleic acid by a method comprising amplifying the HPV nucleic acid with a consensus primer capable of amplifying at least a portion of each of the first, second, and third genotypes of the target nucleic acid.

In an aspect, the target nucleic acid is amplified by a method comprising qualitative PCR.

In an aspect, the target nucleic acid is first identified as being the first, second, or third genotypes of the target nucleic acid by a method comprising hybridizing a consensus probe to the genotypes of the target nucleic acid, wherein the consensus probe is specific for each of the first, second, and third genotypes of the target nucleic acid.

In an aspect, hybridization of the consensus probe to the first, second, and/or third HPV nucleic acids generates a DNA:RNA hybrid.

In an aspect, the DNA:RNA hybrid is detected by a method comprising contacting the DNA:RNA hybrid with a DNA:RNA-specific antibody.

In an aspect, the DNA:RNA hybrid is detected by a method comprising contacting the DNA:RNA hybrid with a DNA:RNA-specific antibody.

In an aspect, the method comprises, consists essentially of, or consists of: (1) performing a qualitative PCR reaction on the sample to obtain an initial indication of the presence of an HR-HPV genotype; (2) performing a hybrid capture assay to confirm a determination of the presence of the HR-HPV; and (3) conducting a PS test to genotype the HR-HPV determined to be present in the sample.

DETAILED DESCRIPTION

The present disclosure covers methods, compositions, reagents, and kits for determining the genotype of at least one HPV nucleic acid in a sample. The methods, compositions, reagents, systems, and kits may be used for clinical diagnostic purposes, including but not limited to the detection and identification of HPV-infected tissue and the determination of the risk of developing a pathological state associated with that HPV infection.

In an aspect, a method for genotyping an HPV nucleic acid in a sample is provided comprising:
  (a) generating a first detection mixture by a method comprising contacting a portion of the sample with a first probe set, wherein the first probe set comprises a nucleic acid probe specific for a first HPV nucleic acid and a nucleic acid probe specific for a second HPV nucleic acid, but does not comprise a nucleic acid probe specific for a third HPV nucleic acid;
  (b) generating a second detection mixture by a method comprising contacting a portion of the sample with a first probe set, wherein the second probe set comprises a nucleic acid probe specific for the second HPV nucleic acid and a nucleic acid probe specific for the third HPV nucleic acid, but does not comprise a nucleic acid probe specific for the first HPV nucleic acid; and
  (c) treating the first and second detection mixtures under conditions wherein the nucleic acid probes hybridize specifically to the first, second, and/or third HPV nucleic acid; and
  (d) detecting hybridization of the nucleic acid probe to the HPV nucleic acid, wherein:
    (i) hybridization in the first detection mixture, but not the second detection mixture indicates that the sample comprises the first HPV nucleic acid;
    (ii) hybridization in the second detection mixture, but not the first detection mixture, indicates that the sample comprises the third HPV nucleic acid; and
    (iii) hybridization in the first detection mixture and the second detection mixture indicates that the sample comprises the second HPV nucleic acid.

A. Samples

Any sample may be used as a starting point, including, without limitation, a specimen or culture (e.g., cellular, microbiological and viral cultures) including clinical and laboratory biological and environmental samples. Biological samples may be from an animal, including a human, fluid, solid (e.g., stool) or tissue, as well as liquid and solid food and feed products and ingredients such as dairy items, vegetables, meat and meat by-products, and waste. Environmental samples include environmental material such as surface matter, soil, water and industrial samples, as well as samples obtained from food and dairy processing instruments, apparatus, equipment, utensils, disposable and non-disposable items.

Exemplary biological samples include, but are not limited to, cervical epithelial cells (e.g., a sample obtained from a cervical swab), adenoid cells, anal epithelial cells, blood, saliva, cerebral spinal fluid, pleural fluid, milk, lymph, sputum and semen.

In an aspect, the biological sample is collected and stored in a collection medium. The collection medium has several functions including as a preservative medium to preserve nucleic acids and inhibit nucleases to prevent degradation of nucleic acids prior to analysis. In one aspect, the collection medium is detergent-based. Without being limited, exemplary collection media include those found in U.S. Patent Publication No. US 2010-0105060 A1 and U.S. Patent Publication No. US 2010-0159463 A1, both of which are hereby incorporated by reference in their entirety.

In one aspect the detergent-based collection medium comprises, consists essentially of, or consists of 1.0% NP-40, 0.25% sodium deoxycholate, 50 mM Tris-HCl, 25 mM EDTA, 150 mM NaCl and 0.05% sodium azide. In another aspect the detergent-based collection medium comprises, consists essentially of, or consists of about 0.5% to about 2.0% NP-40, about 0.10% to about 0.40% sodium deoxycholate, about 25 mM to about 75 mM Tris-HCl, about 10 mM to about 50 mM EDTA, about 50 mM to about 200 mM NaCl, and about 0.01% to about 0.10% sodium azide. In other aspects the detergent-based collection medium comprises, consists essentially of, or consists of about 0.8% to about 1.5% NP-40, about 0.20% to about 0.40% sodium deoxycholate, about 30 mM to about 60 mM Tris-HCl, about 20 mM to about 40 mM EDTA, about 100 mM to about 200 mM NaCl, and about 0.025% to about 0.075% sodium azide. In yet another aspect the detergent-based collection medium comprises, consists essentially of, or consists of about 0.9% to about 1.2% NP-40, about 0.20% to about 0.30% sodium deoxycholate, about 30 mM to about 60 mM Tris-HCl, about 20 mM to about 30 mM EDTA, about 100 mM to about 150 mM NaCl, and about 0.04% to about 0.06% sodium azide.

In an aspect, the collection medium comprises, consists essentially of, or consists of NP-40 and EDTA. In another aspect, the collection medium comprises, consists essentially of, or consists of NP-40, EDTA, and sodium azide. In one aspect, the collection medium comprises, consists essentially of, or consists of sodium deoxycholate, EDTA, and sodium azide. In an aspect, the collection medium comprises, consists essentially of, or consists of about NP-40, sodium deoxycholate, EDTA, and sodium azide. In an aspect, the collection medium comprises, consists essentially of, or consists of NP-40, sodium deoxycholate, Tris-HCl, EDTA, and sodium azide.

In another aspect, the collection medium comprises, consists essentially of, or consists of 0.5% to about 2.0% NP-40 and 10 mM to about 50 mM EDTA. In another aspect, the collection medium comprises, consists essentially of, or consists of 0.5% to about 2.0% NP-40, 10 mM to about 50 mM EDTA, and about 0.01% to about 0.10% sodium azide. In one aspect, the collection medium comprises, consists essentially of, or consists of about 0.10% to about 0.40% sodium deoxycholate, 10 mM to about 50 mM EDTA, and about 0.01% to about 0.10% sodium azide. In an aspect, the collection medium comprises, consists essentially of, or consists of about 0.5% to about 2.0% NP-40, about 0.10% to about 0.40% sodium deoxycholate, 10 mM to about 50 mM EDTA, and about 0.01% to about 0.10% sodium azide. In an aspect, the collection medium comprises, consists essentially of, or consists of about 0.5% to about 2.0% NP-40, about 0.10% to about 0.40% sodium deoxycholate, about 25 mM to about 75 mM Tris-HCl, about 10 mM to about 50 mM EDTA, and about 0.01% to about 0.10% sodium azide. In certain aspects, the medium comprises or consists essentially of 1% NP-40, 0.25% sodium deoxycholate, 50 mM Tris-HCl, 25 mM EDTA, 150 mM NaCl and 0.09% sodium azide. This medium is often referred to herein as Digene Collection Medium or DCM.

Samples may be collected in other known collection mediums and can be used in the methods described herein. Examples of other collection media include PRESERV-CYT®, SUREPATH®, urine, and STM™ (Sample/Specimen Transport Medium). Samples collected in some of these media may require processing before the nucleic acids in the samples can be detected and analyzed. Various methods of processing samples (also known as preparing the samples) are known in the art. For example, cervical cell samples collected for cytological analysis in medium such as PRESERVCYT® may be combined with a detergent-based lysis buffer followed by the addition of magnetic beads comprising nucleic acid binding surfaces.

In another aspect, the sample may comprise, consist, or consist essentially of nucleic acids that have been extracted from a biological sample. Numerous methods are known for extracting nucleic acids from a biological or environmental sample, including but not limited to: phenol/chloroform extraction; anion exchange chromatography; cesium chloride gradient ultracentrifugation; size exclusion chromatography; and silca/chaotropic salt extraction. Extracted nucleic acids may be further separated according to size by gel electrophoresis and extracted from the gel if samples comprising specific nucleic acid sizes are desired.

B. Target Nucleic Acids

As noted above, the methods disclosed herein relate to the detection and genotyping of target nucleic acid in a sample. The target nucleic acid may be DNA or RNA or both DNA and RNA and can be single-stranded, double-stranded, or partially single-stranded. The target nucleic acid can be contained within a larger nucleic acid. Detection of either the target nucleic acid or the larger nucleic acid comprising the target nucleic acid is contemplated by this disclosure.

The target nucleic acids may include, without limitation, nucleic acids found in specimens or cultures (e.g., cellular, microbiological and viral cultures) including biological and environmental samples. The target nucleic acids may be found in biological samples from an animal, including a human, fluid, solid (e.g., stool) or tissue, as well as liquid and solid food and feed products and ingredients such as dairy items, vegetables, meat and meat by-products, and waste. Target nucleic acids may be found in environmental samples and include environmental material such as surface matter, soil, water and industrial samples, as well as samples obtained from food and dairy processing instruments, apparatus, equipment, utensils, disposable and non-disposable items.

The target nucleic acids found in biological samples include, but are not limited to, cervical samples (e.g., a sample obtained from a cervical swab) or cervical cell samples, adenoid cells, anal epithelial cells, blood, saliva, cerebral spinal fluid, pleural fluid, milk, lymph, sputum, urine and semen. The target nucleic acids may be from other viral, bacteria, mycobacteria or plasmodia, such as cytomegalovirus (CMV), herpes simplex virus (HSV), human immunodeficiency virus (HIV), H1N1, *Neisseria gonorrhoeae* (GC), *Chlamydia trachomatis* (CT), *Trichomonas vaginalis, Staphylococcus aureus, mycobacterium tuberculosis*, SARS-associated coronavirus or influenza.

In an aspect the target nucleic acids are at least 75%, at least 80%, at least 85%, at least 90%, at least 95%, at least 96%, at least 97%, at least 98%, at least 98%, at least 99%, or 100% identical to nucleic acids associated with any one of cervical samples (e.g., a sample obtained from a cervical swab) or cervical cell samples, adenoid cells, anal epithelial cells, blood, saliva, cerebral spinal fluid, pleural fluid, milk, lymph, sputum, urine and semen, other viral, bacteria, mycobacteria or plasmodia, for example cytomegalovirus (CMV), herpes simplex virus (HSV), human immunodeficiency virus (HIV), H1N1, *Neisseria gonorrhoeae* (GC), *Chlamydia trachomatis* (CT), *Trichomonas vaginalis, Staphylococcus aureus, mycobacterium tuberculosis*, SARS-associated coronavirus or influenza.

In one aspect, the target nucleic acid is an HPV nucleic acid. In another aspect, the HPV nucleic acid is HPV DNA of a HR-HPV type. In another aspect, the HPV nucleic acid is HPV RNA of a LR-HPV type. In another aspect the target nucleic acids are any one of HR-HPV types 16, 18, 26, 31, 33, 35, 39, 45, 51, 52, 56, 58, 59, 66, 68, and 82 or any one of LR-HPV types 2, 3, 6, 7, 10, 11, 13, 27, 28, 30, 32, 40, 42, 43, 53, 54, 55, 61, 62, 67, 69, 70, 71, 72, 74, 81, 83, 84, 85, 86, 87, 89, 90, and 91.

In another aspect, a plurality of target nucleic acid is targeted. In one aspect, the plurality of target nucleic acids consists of a set of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleic acids having distinct nucleotide sequences. Any set of nucleic acids to be targeted can be used. In one aspect, the plurality of target nucleic acids is selected such that each is related to the others. By way of example and not limitation, the set of nucleic acids can be: structurally related to one another (for example, members of a gene family); functionally related to one another (for example, nucleic acids encoding proinflammatory cytokines); phylogenetically related to one another (for example, nucleic acids specific for different members of a family of viruses, such as HPV-family viruses); related by virtue of differential expression in a different cell or tissue type (for example, macrophage-associated nucleic acids and prostate-associated nucleic acids) or disease states (cervical cancer associated nucleic acids). In another aspect, the set of nucleic acids is unrelated.

In one aspect, a set of target nucleic acids comprises, consists, or consists essentially of HR-HPV types 16, 18, 26, 31, 33, 35, 39, 45, 51, 52, 56, 58, 59, 66, 68, and 82, or any subset thereof. In another aspect, a set of target nucleic acids comprises, consists, or consists essentially of LR-HPV types 2, 3, 6, 7, 10, 11, 13, 27, 28, 30, 32, 40, 42, 43, 53, 54, 55, 61, 62, 67, 69, 70, 71, 72, 74, 81, 83, 84, 85, 86, 87, 89, 90, and 91, or any subset thereof. In another aspect a set of target nucleic acids comprises, consists, or consists essentially of HR-HPV types 16, 18, 26, 31, 33, 35, 39, 45, 51, 52, 56, 58, 59, 66, 68, and 82, or any subset thereof; and LR-HPV types 2, 3, 6, 7, 10, 11, 13, 27, 28, 30, 32, 40, 42, 43, 53, 54, 55, 61, 62, 67, 69, 70, 71, 72, 74, 81, 83, 84, 85, 86, 87, 89, 90, and 91, or any subset thereof. In another aspect, the target nucleic acid is at least 75%, at least 80%, at least 85%, at least 90%, at least 95%, at least 96%, at least 97%, at least 98%, at least 98%, at least 99%, or 100% identical to nucleic acids associated with any one of HPV, genetic variants of HPV, HPV DNA of a HR-HPV type, or HPV RNA of a HR-HPV type. In another aspect the target nucleic acids are at least 75%, at least 80%, at least 85%, at least 90%, at least 95%, at least 96%, at least 97%, at least 98%, at least 98%, at least 99%, or 100% identical to nucleic acids associated with any one of HR-HPV types 16, 18, 26, 31, 33, 35, 39, 45, 51, 52, 56, 58, 59, 66, 68, and 82 or any one of LR-HPV types 2, 3, 6, 7, 10, 11, 13, 27, 28, 30, 32, 40, 42, 43, 53, 54, 55, 61, 62, 67, 69, 70, 71, 72, 74, 81, 83, 84, 85, 86, 87, 89, 90, and 91.

In another aspect, a subset of HPVs may first be identified as candidates for infection, which may then be specifically genotyped by the methods disclosed herein. Numerous tests are commercially available for determining the presence of a high-risk nucleic acid in a sample, such as the HC2® HPV test available from Qiagen Gaithersburg, Inc. Such tests commonly identify a group of HPV nucleic acids which are related by their clinical association with pathological conditions, such as cervical cancer. However, they generally have not been used for specifically genotyping the type of infection.

In one aspect, a set of three target nucleic acids are selected. By way of example and not limitation, HPV 16, HPV 18, and HPV 45 are the three HPV variants most commonly associated with the development of HPV-associated cervical cancer. Thus, the method could comprise first identifying abnormal cervical cells by cytological analysis, confirming the presence of one of HPV 16, HPV 18, or HPV 45 in the sample, and then genotyping according to the methods described herein.

C. Sample Preparation

After the sample is collected in a collection medium as described above, the sample may be treated with a denaturation reagent to render the target nucleic acid accessible to hybridization. In one aspect, the sample is denatured with an alkaline solution. Without being limited, suitable alkali include NaOH and KOH.

Alkaline treatment of protein effectively homogenizes the specimen to ensure reproducibility of analysis results for a given sample. It can also reduce the viscosity of the sample to increase kinetics, homogenize the sample, and reduce background by destroying any endogenous single stranded RNA nucleic acids, DNA-RNA hybrids or RNA-RNA hybrids in the sample. It also helps inactivate enzymes such as RNases and DNases that may be present in the sample. One skilled in that art would appreciate that if RNA is the target nucleic acid (as opposed to DNA), different reagents may be preferable including, but not limited to phenol extraction and TCA/acetone precipitation, and guanidinium thiocyanate-phenol-chloroform extraction.

Other methods of denaturation may be employed such as utilizing a heating step, for example, heating the sample to about 95° C. to separate the strands of nucleic acid. Enzymes such as helicase may be used as well.

D. Detection Mixtures

After the sample comprising the nucleic acid is prepared for hybridization, it is separated into two aliquots, each of which is contacted with a probe set comprising at least one polynucleotide probe specific for each genotype of target nucleic acid being tested under a condition sufficient for the probes to hybridize to the at least one target nucleic acid in the sample. The at least one polynucleotide probe can be full length, truncated, or synthetic DNA or full length, truncated, or synthetic RNA.

In an aspect, a plurality of polynucleotide probes for each is used for each genotype. In one aspect, 2, 3, 4, 5, 6, 7, 8, 9, or 10 polynucleotide probes may be provided that are specific for each genotype. In another aspect, each polynucleotide probe is selected such that it is specific only for one genotype and does not cross-react with any other target nucleic acids in stringent conditions. In yet another aspect, at least two polynucleotide probes are provided for each genotype, wherein each polynucleotide probe hybridizes to a distinct region of the target nucleic acid. By way of example, where the target nucleic acids comprise HPV nucleic acids, at least one polynucleotide may be chosen for each of the E6/E7 and L1 regions of the HPV nucleic acid.

In one aspect, the polynucleotide probe is used to purify the target nucleic acid before detection. In such a case, each polynucleotide probe may be specific for only a single genotype or may be designed so as to hybridize to a each genotype being targeted in the detection mixture under stringent conditions. By way of example and not limitation, a polynucleotide probe may be designed against a highly conserved region of nucleic acids encoding a specific gene product, such that the polynucleotide probe would be expected to hybridize under stringent conditions to substantially all nucleic acids encoding that gene product.

In an aspect, the polynucleotide probe is capable of hybridizing or binding to nucleic acids at least 75%, at least 80%, at least 85%, at least 90%, at least 95%, at least 96%, at least 97%, at least 98%, at least 98%, at least 99%, or 100% identical to nucleic acids associated with HPV, genetic variants of HPV, HPV DNA of a HR-HPV type, or HPV RNA of a HR-HPV type, or any one of one of HR-HPV types 16, 18, 26, 31, 33, 35, 39, 45, 51, 52, 56, 58, 59, 66, 68, and 82 or any one of LR-HPV types 2, 3, 6, 7, 10, 11, 13, 27, 28, 30, 32, 40, 42, 43, 53, 54, 55, 61, 62, 67, 69, 70, 71, 72, 74, 81, 83, 84, 85, 86, 87, 89, 90, and 91. In another aspect, the probe is complementary to HPV, genetic variants of HPV, HPV DNA of a HR-HPV type, HPV RNA of a HR-HPV type, or any one of one of HR-HPV types 16, 18, 26, 31, 33, 35, 39, 45, 51, 52, 56, 58, 59, 66, 68, and 82 or any one of LR-HPV types 2, 3, 6, 7, 10, 11, 13, 27, 28, 30, 32, 40, 42, 43, 53, 54, 55, 61, 62, 67, 69, 70, 71, 72, 74, 81, 83, 84, 85, 86, 87, 89, 90, and 91.

In another aspect, a plurality of polynucleotide probes is provided, the plurality being selected to hybridize to and purify each genotype being targeted in the detection mixture. In one aspect, the plurality of polynucleotide probes is capable of hybridizing to each nucleic acid of a set of target nucleic acids consisting of HR-HPV types 16, 18, 26, 31, 33, 35, 39, 45, 51, 52, 56, 58, 59, 66, 68, and 82 nucleic acids, or any subset thereof. In one aspect, the plurality of polynucleotide probes is capable of hybridizing to each nucleic acid of a set of target nucleic acids consisting of LR-HPV types 2, 3, 6, 7, 10, 11, 13, 27, 28, 30, 32, 40, 42, 43, 53, 54, 55, 61, 62, 67, 69, 70, 71, 72, 74, 81, 83, 84, 85, 86, 87, 89, 90, and 91, or any subset thereof. In one aspect, the plurality of polynucleotide probes is capable of hybridizing to each nucleic acid of a set of target nucleic acids consisting of HR-HPV types 16, 18, 26, 31, 33, 35, 39, 45, 51, 52, 56, 58, 59, 66, 68, and 82, or any subset thereof; and LR-HPV types 2, 3, 6, 7, 10, 11, 13, 27, 28, 30, 32, 40, 42, 43, 53, 54, 55, 61, 62, 67, 69, 70, 71, 72, 74, 81, 83, 84, 85, 86, 87, 89, 90, and 91, or any subset thereof.

If the target nucleic acid was denatured using an alkaline treatment, the one or more polynucleotide probes may be diluted in a probe diluent that also can act as a neutralizing hybridization buffer (to neutralize the basic denaturation reagent).

The probe diluent used for DNA or RNA probes will differ due to the different requirements necessary for DNA versus RNA stability. For example, if the probes are RNA, it is preferable to neutralize the sample first and then add the probe or alternatively, add the RNA probe and neutralizing agent (probe diluent) to the sample at the same time as excessive alkalinity can destroy RNA. The probe diluent can be used to dissolve and dilute the probe and also help restore the sample to about a neutral pH, e.g., about pH 6 to about pH 9, to provide a more favorable environment for hybridization. Sufficient volume of probe diluent, preferably one-half volume of the sample, may be used to neutralize the base-treated sample.

For full length probes, a heated alkaline solution may be added to the sample, then probe diluent may be added to the sample at room temperature, and then the sample may be reheated. Such a process can inhibit secondary structure from forming. Antibodies tend to irreversibly bind to structures with secondary structure. When using non-full length probes such as truncated or synthetic probes, heating the solutions or sample may not be necessary because secondary structures issues are not present. In an aspect, the sample is not heated when used with truncated or synthetic probes.

After treatment with the denaturation reagent, an aliquot of neutralization buffer, in an aspect the probe diluent described, in which the one or more probes are dissolved, can be added to the sample under appropriate conditions to allow hybridization or binding of the probe and the at least one target nucleic acid to occur. The neutralization buffer may contain a single buffering salt. In an aspect, the neutralization buffer does not contain more than a single buffering salt. The hybridization condition is sufficient to allow the one or more polynucleotide probes to anneal to a corresponding complementary nucleic acid sequence, if present, in the sample to form a double-stranded nucleic acid hybrid.

Hybridization conditions suitable for the particular probes and diluents described herein are employed. For example, the probes and sample nucleic acids can be incubated for a hybridization time, preferably at least about 5 to about 30 minutes, about 5 to about 20 minutes, or from about 7 to about 15 minutes, or about 10 minutes, as well as any number within the recited ranges sufficient to allow the one or more polynucleotide probes to anneal to a corresponding complementary nucleic acid sequence. The hybridization condition can include a hybridization temperature of at least about 65° C., about 68.5° C., and about 67° C. to about 70° C., as well as any number within the recited ranges. For a given at least one target nucleic acid and a given probe, one of ordinary skill in the art can readily determine desired hybridization conditions by routine experimentation. One of ordinary skill in the art will further appreciate that the time and temperature of hybridization must be optimized, one with respect to the other. Thus, higher hybridization temperatures may be carried out for shorter periods of time and vice versa. Without being limited, stringent hybridization conditions may be controlled by increasing the temperature, increasing the ionic conditions to above 0.5M (for example, NaCl), or reducing the concentration of PAA. As a non-limiting example, stringent hybridization conditions may include performing a hybridization reaction at elevated temperatures, such as of at least about 65° C., at least about 68.5° C., between about 67° C. to about 70° C., and between about 69° C. to about 70° C. Stringent hybridization conditions may also include elevated temperatures, such as of at least about 65° C., at least about 68.5° C., and between about 67° C. to about 70° C. An extensive guide to the hybridization of nucleic acids is found in Tijssen, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, N.Y. (1993); and Current Protocols in Molecular Biology, Chapter 2, Ausubel, et al., Eds., Greene Publishing and Wiley-Interscience, New York (1995), incorporated by reference in its entirety.

For present purposes, "stringent conditions" encompass conditions under which hybridization will only occur if there is 25% mismatch or less between the hybridization molecule and the target sequence. "Stringent conditions" may be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize. Calculations regarding hybridization conditions required for attaining particular degrees of stringency are also discussed by Sambrook et al. (ed.), Molecular Cloning: A Laboratory Manual, 2nd ed., vol. 1-3, Cold Spring Harbor Laboratory Press, Cold Spring Harbor, N.Y., 1989, chapters 9 and 11, herein incorporated by reference in its entirety.

In an aspect, the hybridization step is completed at 50° C. in about 15-25 minutes; at 50° C. in about 20-25 minutes; or at 50° C. in about 22.5 minutes.

In one aspect, each detection mixture is formed by suspending the sample in collection medium, denaturing the target nucleic acid with a denaturation reagent, and hybridizing the target nucleic acid to nucleic acid probes suspended in a neutralizing buffer. In another aspect the neutralizing buffer is a probe diluent comprising 2.2 M BES (N,N-bis(2-hydroxyethyl)-2-aminoethanesulfonic acid), 2.6% polyacrylic acid, 0.7 N NaOH and 0.05% sodium azide.

E. Detection

After the probes are allowed to hybridize to the at least one target nucleic acid and form a double-stranded nucleic acid hybrid, the hybrid is detected.

In an aspect, the hybrid is first immobilized to a solid phase before detection. Following immobilization of the hybrid to the solid phase, the captured hybrid may be separated from the rest of the sample by washing away of non-captured nucleic acids. The nucleic acid hybrid is then detected.

In one aspect, the probes are either immobilized to a solid phase (such as by covalent bonding) or adapted to be immobilized to a solid phase (such as via streptavidin-biotin interactions). In such a case, hybridization of the nucleic acid probe to the target nucleic acid will result in the target nucleic acid being immobilized to solid phase.

In another aspect, the nucleic acid probe is not immobilized or adapted to be immobilized to a solid phase. In such a case, the hybrid may be immobilized to a solid phase by contacting it with an anti-hybrid antibody. In another aspect, the anti-hybrid antibodies are immobilized onto a support before the double-stranded nucleic acid hybrid is captured. Methods of immobilizing antibodies to solid supports are well known in the art. By way of example and not limitation, the antibodies can be covalently linked to the solid support. As another example, the antibody can be adsorbed onto the solid phase via, for example, protein-protein interactions, protein-G beads, biotin-streptavidin interaction, EDAC to link to a carboxyl or tosyl group, etc., or hybridization directly onto the solid support using, for example, sequence specific nucleic acids in an affinity column. In another aspect, the anti-hybrid antibodies may be complexed with the double-stranded nucleic acid hybrid before being immobilized on the solid support. By way of example and not limitation the anti-hybrid antibody may be conjugated with a biotin label, while the support may be conjugated with a streptavidin moiety. Anti-hybrid antibody/double-stranded nucleic acid-hybrid complexes can then be allowed in the absence of the solid support. When the solid support is added to the reaction mixture, the anti-hybrid antibody/double-stranded nucleic acid-hybrid complexes will be immobilized to the solid support by virtue of the interaction between the biotin conjugate and the streptavidin moiety.

Once immobilized, detection may then be performed.

In one aspect, the hybrid can be detected by hybridizing a detectably labeled second nucleic acid probe to the target nucleic acid. In another aspect, the hybrid is detected by contacting it with a molecule that binds specifically to double-stranded nucleic acid hybrids. Molecules specific for the double-stranded nucleic acid hybrids include, but are not limited to, monoclonal antibodies, polyclonal antibodies, proteins such as but not limited to RNAse H, nucleic acids including but not limited to aptamers, or sequence specific nucleic acids. Aptamers are short stretches of random sequences that are successively selected from a library of sequences by hybridizing to a target, amplifying the hybridized aptamers, and repeating the selection process. The molecule that binds specifically to double-stranded nucleic acid hybrids may be detectably labeled.

In one aspect, the probe forms a DNA:RNA hybrid with the target nucleic acid when hybridized thereto. In such a circumstance, the immobilized hybrid may be detected using an antibody that is specific for double-stranded DNA:RNA hybrids. The antibody may be detectably labeled, either directly or indirectly, and may be a monoclonal or polyclonal antibody. In an aspect, the antibody is monoclonal. In another aspect, the antibody is directly labeled with a detectable marker and is monoclonal. In one aspect, the antibody has a label that must react with a substrate to provide a signal that can be detected. The antibody may be dissolved in a suitable buffer. In one aspect the buffer comprises 100 mM TrisHCl, pH 7.4, 0.5 M NaCl, 0.1 mM ZnCl2, 1.0 mM MgCl2, 0.25% TWEEN 20™, 0.2 mg/ml RNase A, 4% hydroxypropyl-b-cyclodextrin (cyclodextrin), 30% bead dilution buffer as discussed previously, 0.05% goat IgG, 0.05% sodium azide.

In one aspect, the probe forms a DNA:RNA hybrid with the target nucleic acid when hybridized thereto, is immobilized to the solid phase using an antibody that is specific for double-stranded DNA:RNA hybrids, and is detected with a second antibody specific for a double-stranded DNA:RNA hybrid.

Solid supports include but are not limited to beads; magnetic beads, including paramagnetic, diamagnetic, ferromagnetic, ferromagnetic, and diamagnetic beads, columns, plates, filter paper, polydimethylsiloxane (PDMS); dipsticks; coated tubes, plates, and dishes; and resin columns. Any support can be used as long as it allows extraction of the liquid phase and provides the ability to separate out bound and unbound antibodies. Paramagnetic beads are particularly useful in that they can be left in the solution and the liquid phase can be extracted or decanted, if a magnetic field is applied to immobilize the beads. Beads that are small and have a high surface area are preferable, such as beads about 1 μm in diameter. Other beads that employ charge switching or silica capture (as opposed to magnetic fields) may be used as well.

In an aspect, the hybrids are incubated with the anti-hybrid antibody attached to the support for a sufficient amount of time to allow capture of the double-stranded nucleic acid hybrids by the immobilized anti-hybrid antibodies. In an aspect, the support is a bead. The anti-hybrid antibody may be monoclonal or polyclonal. In one aspect the antibody is monoclonal. In one aspect, the antibody is coupled to the support by a 1-ethyl-3-[3-dimethylaminopropyl]carbodiimide hydrochloride (EDAC) linker. In one aspect, the support is a polystyrene bead. In an aspect, the support or bead coupled to the antibody is diluted in a bead dilution buffer. The bead dilution buffer is helpful in minimizing protein denaturation on the bead. One example of a bead dilution buffer comprises 6% casein, 100 mM TrisHCl, 300 mM NaCl, and 0.05% sodium azide.

In an aspect, the beads coated with the anti-hybrid antibody are incubated with the sample at about 67° C. to about 70° C. for about 30 minutes. In another aspect, the beads and sample are incubated at about 68° C. to about 69° C. for about 30 minutes. In yet another aspect, the beads and sample are incubated at about 68.5° C. for 30 minutes. The incubation time can range from about 5 minutes to about 60 minutes, from about 15 minutes to about 45 minutes, from about 20 minutes to about 40 minutes, or any number within the recited ranges, and is generally inversely proportional to the temperature. It will be understood by those skilled in the art that the incubation time, temperature and/or shaking conditions can be varied to achieve alternative capture kinetics as desired.

It will be understood by those skilled in the art that any detectable label such as, but not limited to, an enzyme, radioactive molecule, fluorescent molecule, or metal particle such as gold particle can be used. In certain aspects, the detectable label may be alkaline phosphatase. Methods of conjugating a label to an antibody are known. For example, an antibody can be reduced with dithiothreitol (DTT) to yield monovalent antibody fragments. The reduced antibody can then be directly conjugated to maleinated alkaline phosphatase by the methods of Ishikawa et al., J. Immunoassay 4:209-237 (1983) and Means et al., Chem. 1: 2-12 (1990), the contents of each of which are incorporated herein by reference in its entirety, and the resulting conjugate can be purified by HPLC. The conjugate may also be purified using any type of size-exclusion chromatography. One benefit of purification is that the conjugates of one protein to one antibody can be separated from those conjugates with other ratios of protein to antibody.

In another aspect, the double-stranded nucleic acid hybrids can be detected with a second anti-hybrid antibody that is not directly labeled. For example, the second antibody can be a mouse immunoglobulin that is detected by a labeled goat anti-mouse antibody.

The label present on the labeled solid support may be used to identify the particular genotype of the target nucleic acid. The label on the probe or detection antibody may convey information about the quantity of each target nucleic acid purified and may, in addition, convey additional information about the genotype of the target nucleic acids.

Methods for detecting various labels are known in the art. For example, colorimetry, radioactive, surface plasmon resonance, or chemiluminescence methods are described by e.g., Coutlee et al., J. Clin. Microbiol. 27:1002-1007 (1989), the contents of which are incorporated herein by reference in its entirety. For example, a bound alkaline phosphatase conjugate can be detected by chemiluminescence with a reagent such as a LUMI-PHOS 530 reagent (Lumigen, Detroit, Mich.) or DR2 (Applied Biosystems, Foster City, Calif.) using a detector such as an E/LUMINA luminometer (Source Scientific Systems, Inc., Garden Grove, Calif.), an OPTOCOMP I Luminometer (MGM Instruments, Hamden, Conn.), or the like, such as a Veritas Microplate Luminometer by Turner Biosystems. Multiple detection techniques can also be used in sequence or in parallel. For example, the conjugate may be detected by chemiluminescence and fluorescence. In another aspect, the conjugate can be detected by chemiluminescence.

Detectors using different detection techniques for the conjugate may be reversible or irreversibly attached, for example in a modular fashion, to a machine that is capable of performing the method for determining the presence of at least one target nucleic acid in a sample.

All probes used herein may be short synthetic RNA probes that specifically bind only to the at least one target nucleic acid. Examples are described in U.S. Patent Application Publication No. US 2009-0298187 A1, the contents of which are incorporated herein by reference in its entirety.

The present disclosure also provides for assay compositions, probes, and conditions wherein cross-reactivity between HR-HPV probe sets and LR-HPV types is dramatically reduced when compared to the standard FDA approved HPV assay and probe set. In one aspect, the HPV high-risk probe set is selected from the group consisting of HPV high-risk types 16, 18, 31, 33, 35, 39, 45, 51, 52, 56, 58, 59, 66, 68, and 82 or LR-HPV types 2, 3, 6, 7, 10, 11, 13, 27, 28, 30, 32, 40, 42, 43, 53, 54, 55, 61, 62, 67, 69, 70, 71, 72, 74, 81, 83, 84, 85, 86, 87, 89, 90, and 91. Using the present assay with these HR-HPV probes, cross-reactivity between LR-HPV types and HR-HPV probes is reduced. See, for example, U.S. Patent Application Publication No. US 2009-0298187 A1.

The present disclosure also provides methods and assays for detecting cancer, for example cervical cancer, by detecting the presence of a at least one target nucleic acid, such as HPV, in a sample.

It will be understood to those skilled in the art that the present invention can be carried out on a number of platforms including, but not limited to, tubes, dipsticks, microarrays, microplates, 384 well plates, other microtiter plates and microfluidic systems. It will be understood to those skilled in the art that the present, as relevant to developing countries, can utilize low technology methods such as dropper bottles, rubber bulbs, Pasteur pipettes, or squirt bottles for steps involving movement of liquid. These devices deliver relatively precise volumes within the approximate ranges that are needed for the assay. In an aspect, the methods of the disclosure do not include automatic pipettors or other battery powered or energy powered pipetting devices.

EXAMPLES

I. SP Samples

The reflex genotyping PS™ test is a non-target amplification platform for genotyping samples that have been qualitatively determined to be HR-HPV positive. Sample input volume for the PS™ test is identical to the sample input volume required for the HC2™ screening test for STM™, PC, and SUREPATH® media. Sample preparation for the LBC media is also identical to the preparation required for performing the HC2™ test. To demonstrate compatibility of the SUREPATH® media with the Genotyping PS test, SUREPATH® cervical specimens were used. In addition, to demonstrate equivalence between STM™ and SUREPATH® solution specimens, recovery of HPV target, in each of the media, was examined and compared.

It was demonstrated with SUREPATH® clinical specimens that the PS™ test is not only compatible with STM™ and PC but also with the SUREPATH® media. The PS test detected HPV 16, 18, and/or 45 infections at 5000 copies per assay or greater in the SUREPATH® clinical specimens with the results being confirmed by qPCR. In addition, the results demonstrated that recovery of HPV DNA is equivalent for STM™ and SUREPATH® media. Each specimen type was processed according to its respective processing/denaturation procedures and tested with the PS™ test.

The compatibility of the HPV Genotyping ProbeSet Test (PS™) with SUREPATH® specimen was evaluated with quantitative PCR (qPCR) used as the reference or confirmatory method.

The HC2™ Test is used to generate a qualitative signal for whether a sample contains a high-risk human papillomavirus (HR-HPV) in the cervical specimens. The HC2™ test was performed on 700 μL of SUREPATH® specimen. There were 50 HC2™ positive and 10 HC2™ negative specimens identified and used in this study.

From each sample, a 250 μL aliquot of crude SUREPATH® was transferred to a micro-centrifuge tube for DNA isolation. Cells were pelleted by centrifugation and resuspended in 200 μL of 100 mM Tris pH 8.0. A buffer solution containing an 80:20 ratio of Buffer ATL™ and Proteinase K was added to each sample. The samples were incubated at 60° C. for two hours with shaking at 600 rpm. Following digestion with Proteinase K, samples were processed using the QIAamp® MinElute® Virus Spin kit in accordance with the manufacturer's protocol. QPCR analysis was performed as the reference method, in three separate PCR reactions, to determine the presence and viral load of HPV 16, 18, and/or 45.

The remaining SUREPATH® volume (~1850 μL) after the HC2™ Test and sample prep for qPCR was pelleted by centrifugation. The supernatant was discarded and the cells were resuspended in 150 μL of STM™ and 75 μL of Denaturation Reagent. Subsequently, 75 μL was transferred into three separate wells to identify the genotype individually. Samples were denatured and the DNA:RNA hybrids were captured onto HC2™ capture plates and detected via proprietary hybrid-specific antibodies conjugated with alkaline phosphatase. Finally, a chemiluminescent substrate was added, and the wells were read on a luminometer to measure the Relative Light Units (RLU). Samples were classified as positive for the genotype if the RLU value/cut-off (RLU/CO) value was greater than or equal to 1.3. The cut-off value is determined by the mean of the assay positive calibrator. Results are shown in Table 1:

TABLE 1

| RLU/CO | PS Test Results | qPCR Test Results | Discordants |
|---|---|---|---|
| 0.8-0.9 | 5 | 0 | 0 |
| 1.0-1.2 | 2 | 0 | 0 |
| 1.3-1.9 | 4 | 0 | (4) |
| 2.0-4.9 | 3 | 2 | (1) |
| >5.0 | 13 | 12 | (1) |

A total of 16 of the specimens tested positive specimens with the PS test, with a total of 20 positive results, including 4 multiple infection. Of all the samples tested, 56 out of 60 (93.3%) specimen results according to the PS test agreed with the qPCR (4 discordants) and 174/180 (96.7%) of the genotype result agreed with qPCR (6 discordant). All discordant results are PS positive and qPCR negative.

II. PreservCyt Samples

The intended use of the PS™ Test is to detect multiple HPV genotypes separately, which requires multiple aliquots of each patient specimen. After HC2™ testing, some PC specimens may lack sufficient volume for number of tests desired. Employing probe cocktailing may limit the number of tests required and provide an alternative solution that significantly reduces the specimen input volume.

There were 28 HC2™ positive PC specimens utilized in this study. Following the standard HC2 conversion protocol for the media, 12 ml of PC specimen were processed. PS™ testing was performed simultaneously on six aliquots from each denatured specimen. Three tests detected HPV 16, 18 and 45 separately, using three individual probe mixes with each probe mix containing only one type-specific probe. Three additional tests were performed on each specimen to detect for two or more of the genotypes together. To detect for more than one target in a single test, two or three of the individual probes were combined into a single mix. Multi-probe cocktails were used to detect HPV 16 and 18 together, HPV 18 and 45 together, and all three types in one test. Analytical performance was evaluated by using a probe cocktail to detect HPV plasmid at a concentration of 2 pg/ml. Results are expressed as relative light units to cut-off (RLU/CO). Experiments were conducted according to the scheme set forth in Table 2

TABLE 2

| | PC Specimen Input Volume | | |
|---|---|---|---|
| | 6 mL | 4 mL | 2 mL |
| # of Test Options Genotyping Result | 3 Separate for HPV 16, 18, 45 | 2 HPV 16 alone, HPV 18 & 45 together* | 1 HPV 16, 18, 45 combined |
| # of Probe Mixes Needed | 3 | 2 | 1 |

| | Probe Mix Components for each Test | | | | | |
|---|---|---|---|---|---|---|
| | Mix 1 | Mix 2 | Mix 3 | Mix 1 | Mix 2 | Mix 1 |
| HPV 16 Probe Volume (μl) | 1 | — | — | 1 | — | 1 |
| HPV 18 Probe Volume (μl) | — | 1 | — | — | 1 | 1 |
| HPV 45 Probe Volume (μl) | — | — | 1 | — | 1 | 1 |
| Probe Diluent Volume (μl) | 24 | 24 | 24 | 24 | 23 | 22 |
| 5.5% NP-40 Volume (μl) | 10 | 10 | 10 | 10 | 1 0 | 10 |
| Total Volume (μl) per Test | 35 | 35 | 35 | 35 | 35 | 35 |

*Method can be applied to test for HPV 16 & 18 together, HPV45 alone.

Figure 1:
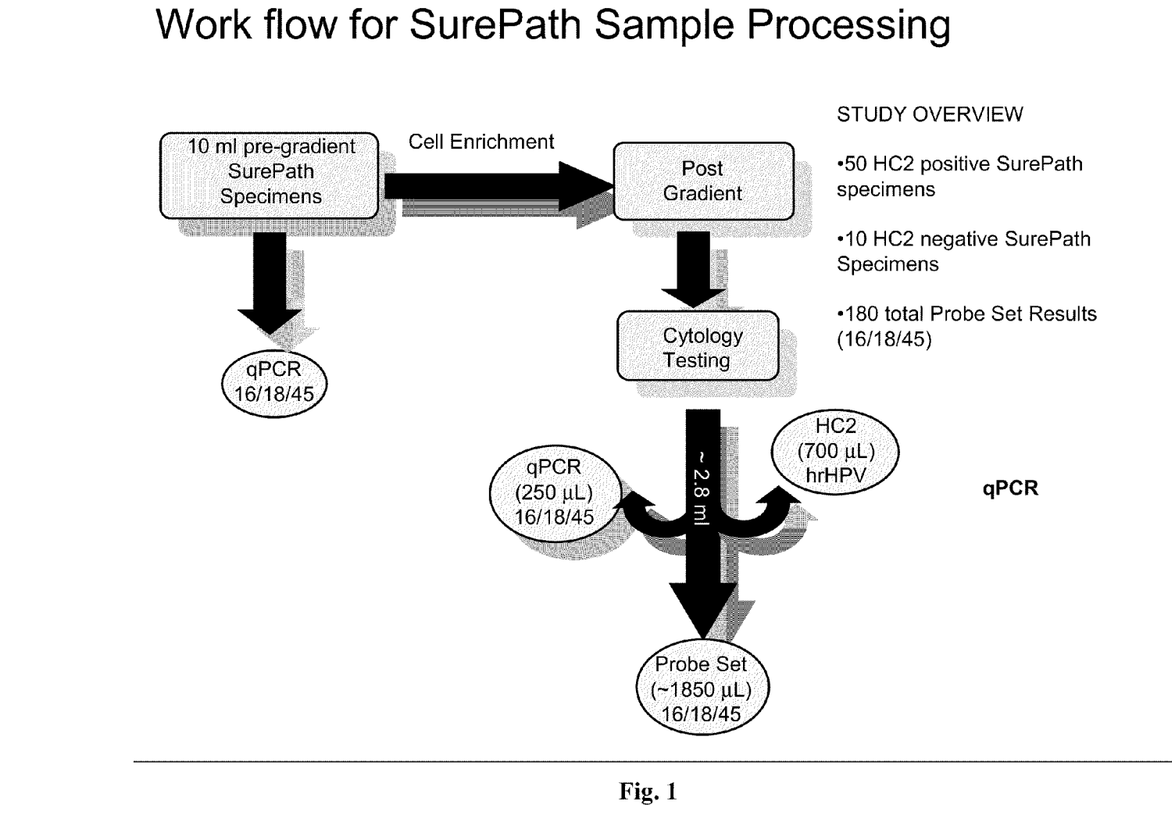
FIG. 1 demonstrates an exemplary workflow for determining the presence of an HPV in a sample.
Figure 2:
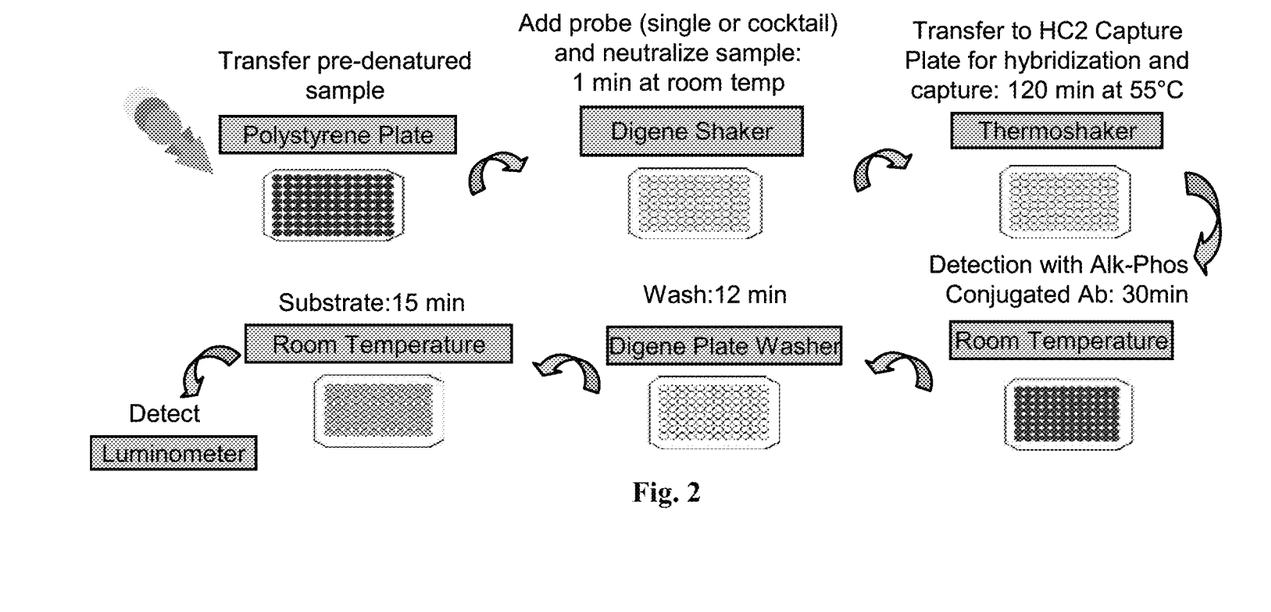
FIG. 2 shows an exemplary workflow for performing a PS test.
Figure 3:
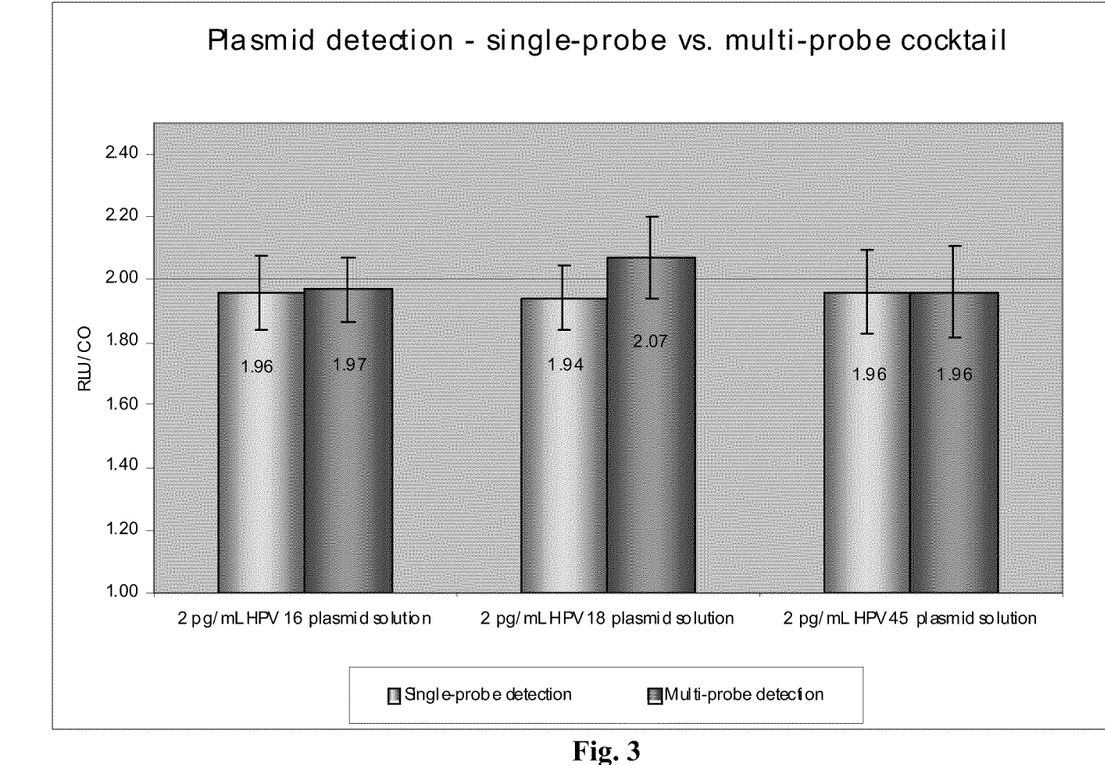
FIG. 3 compares multi-probe mixes with single probe mixes for sensitivity of detection of plasmid DNA at 2 pg/mL concentration.

There were 28 HC2™ positive PC specimens tested for HPV 16, 18 and 45 using the PS™ Test. Each specimen was tested using individual probes for type-specific detection and probe cocktails to detect two or more HPV genotypes together. Results were concordant for all specimens. Of the 28 HC2™ positive samples, 18 were negative for HPV 16, 18 and 45. Data presented in Table 2 details the HPV 16, 18 and 45 positive specimen results. A positive result has an RLU/CO value greater than or equal to 1.3. Data presented in FIG. 3 demonstrates the equivalent sensitivity of multi-probe detection of individual HPV types as compared to single probe detection.

TABLE 3

| | Genotype(s) Detected | | | | | |
|---|---|---|---|---|---|---|
| | HPV 16 Only | HPV 18 Only | HPV 45 Only | HPV 16 and 18 | HPV 18 and 45 | HPV 16, 18 and 45 |
| Specimen Number | Single-Probe Detection | | | Multi-Probe Detection | | |
| | | | PS test RLU/CO | | | |
| 1 | 4625.10 | 0.55 | 0.54 | 578.42 | 0.55 | 1365.15 |
| 2 | 381.22 | 0.52 | 0.50 | 138.20 | 0.47 | 135.56 |
| 3 | 535.24 | 0.18 | 0.20 | 504.69 | 0.34 | 505.78 |
| 4 | 27.34 | 0.12 | 0.10 | 10.76 | 0.13 | 322.28 |
| 5 | 0.28 | 43.59 | 0.28 | 35.86 | 46.77 | 56.44 |
| 6 | 0.24 | 156.02 | 0.22 | 111.24 | 120.38 | 113.22 |
| 7 | 0.34 | 5.14 | 0.22 | 7.72 | 9.12 | 10.26 |
| 8 | 0.59 | 0.39 | 8.81 | 0.39 | 8.31 | 4.99 |
| 9 | 40.72 | 42.21 | 0.34 | 79.75 | 46.79 | 79.84 |
| 10 | 69.89 | 0.14 | 8.89 | 57.20 | 11.63 | 65.81 |

What is claimed is:

1. A method for genotyping a target nucleic acid in a sample is provided comprising:
   (a) generating a first detection mixture by a method comprising contacting a portion of the sample with a first probe set, wherein the first probe set comprises a nucleic acid probe specific for a first genotype of the target nucleic acid and a nucleic acid probe specific for a second genotype of the target nucleic acid, but does not comprise a nucleic acid probe specific for a third genotype of the target nucleic acid;
   (b) generating a second detection mixture by a method comprising contacting a portion of the sample with a second probe set, wherein the second probe set comprises a nucleic acid probe specific for the second genotype of the target nucleic acid and a nucleic acid probe specific for the third genotype of the target nucleic acid, but does not comprise a nucleic acid probe specific for the first genotype of the target nucleic acid; and
   (c) treating the first and second detection mixtures under conditions wherein the nucleic acid probes hybridize specifically to the first, second, and/or third genotype of the target nucleic acid; and
   (d) detecting hybridization of the nucleic acid probe to the target nucleic acid, wherein:
      (i) hybridization in the first detection mixture, but not the second detection mixture indicates that the sample comprises the first genotype of the target nucleic acid;
      (ii) hybridization in the second detection mixture, but not the first detection mixture, indicates that the sample comprises the third genotype of the target nucleic acid; and
      (iii) hybridization in the first detection mixture and the second detection mixture indicates that the sample comprises the second genotype of the target nucleic acid.

2. The method of claim 1 wherein the target nucleic acid is an HPV nucleic acid and the first, second, and third genotypes of the target nucleic acid are selected from the group consisting of HPV2, HPV3, HPV6, HPV10, HPV 11, HPV16, HPV18, HPV26, HPV27, HPV28, HPV29, HPV30, HPV31, HPV32, HPV33, HPV34, HPV35, HPV39, HPV42, HPV45, HPV51, HPV52, HPV53, HPV54, HPV56, HPV57, HPV58, HPV59, HPV64, HPV66, HPV67, HPV68, HPV69, HPV70, HPV73, HPV82, HPV84, HPV85, HPV86, HPV87, and HPV94.

3. The method of claim 2 wherein the first, second, and third genotypes of the target nucleic acid are HPV16, HPV18, and HPV45.

4. The method of claim 1 wherein the sample is a clinical sample preserved in a liquid based cytology medium.

5. The method of claim 4 wherein the liquid based cytology medium is selected from the group consisting of PRESERVCYT and SUREPATH.

6. The method of claim 1 wherein hybridization of the nucleic acid probe forms a DNA:RNA hybrid.

7. The method of claim 6 wherein DNA:RNA hybrid is detected by a method comprising contacting the DNA:RNA hybrid with a DNA:RNA-specific antibody.

8. The method of claim 1 wherein the target nucleic acid is first identified as being the first, second, or third genotypes of the target nucleic acid by a method comprising amplifying the target nucleic acid with a consensus primer capable of amplifying at least a portion of each of the first, second, and third genotypes of the target nucleic acid.

9. The method of claim 8 wherein the target nucleic acid is amplified by a method comprising qualitative PCR.

10. The method of claim 1 wherein the target nucleic acid is first identified as being the first, second, or third genotypes of the target nucleic acid by a method comprising hybridizing a consensus probe to the target nucleic acid, wherein the consensus probe is specific for each of the first, second, and third genotypes of the target nucleic acid.

11. The method of claim 10 wherein hybridization of the consensus probe to the first, second, and/or third HPV nucleic acids generates a DNA:RNA hybrid.

12. The method of claim 11 wherein DNA:RNA hybrid is detected by a method comprising contacting the DNA:RNA hybrid with a DNA:RNA-specific antibody.

13. The method of claim 6 wherein DNA:RNA hybrid is detected by a method comprising contacting the DNA:RNA hybrid with a DNA:RNA-specific antibody.

14. The method of claim 1 comprising: (1) performing a qualitative PCR reaction on the sample to obtain an initial indication of the presence of an high risk-HPV genotype; (2) performing a hybrid capture assay to confirm a determination of the presence of the HR-HPV; and (3) conducting a PS test to genotype the high risk-HPV determined to be present in the sample.

* * * * *